US010214750B2

(12) United States Patent
Borenstein et al.

(10) Patent No.: US 10,214,750 B2
(45) Date of Patent: Feb. 26, 2019

(54) SYSTEMS AND METHODS FOR CELL TRANSDUCTION

(71) Applicant: The Charles Stark Draper Laboratory, Inc., Cambridge, MA (US)

(72) Inventors: Jeffrey T. Borenstein, Newton, MA (US); Joseph L. Charest, Cambridge, MA (US); Christopher M. DiBiasio, Stoughton, MA (US); Dorit Berlin, Lexington, MA (US); Jenna Balestrini, Boston, MA (US); Jose A. Santos, Westwood, MA (US); Vishal Tandon, Roxbury Crossing, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/614,421

(22) Filed: Jun. 5, 2017

(65) Prior Publication Data
US 2017/0349912 A1 Dec. 7, 2017

Related U.S. Application Data

(60) Provisional application No. 62/421,784, filed on Nov. 14, 2016, provisional application No. 62/346,031, filed on Jun. 6, 2016.

(51) Int. Cl.
C12M 1/42 (2006.01)
C12N 15/87 (2006.01)
C12M 1/00 (2006.01)
C12M 1/12 (2006.01)
C12N 5/0783 (2010.01)
B01L 3/00 (2006.01)

(52) U.S. Cl.
CPC ........ *C12N 15/87* (2013.01); *B01L 3/502746* (2013.01); *C12M 23/40* (2013.01); *C12M 25/00* (2013.01); *C12M 27/18* (2013.01); *C12M 29/04* (2013.01); *C12M 35/08* (2013.01); *C12N 5/0636* (2013.01); *B01L 3/502761* (2013.01); *B01L 2200/0668* (2013.01); *B01L 2300/087* (2013.01); *B01L 2300/0877* (2013.01); *B01L 2400/0487* (2013.01); *B01L 2400/086* (2013.01); *C12N 2510/00* (2013.01)

(58) Field of Classification Search
None
See application file for complete search history.

(56) References Cited

U.S. PATENT DOCUMENTS 5,534,423 A 7/1996 Palsson et al.
5,672,494 A 9/1997 Palsson et al.
5,866,400 A 2/1999 Palsson et al.
2004/0259076 A1* 12/2004 Farrow ................. B01D 61/18
435/5
2014/0197105 A1 7/2014 Dibiasio et al.
2014/0287509 A1 9/2014 Sharei et al.

FOREIGN PATENT DOCUMENTS

WO 2013126556 A1 8/2013

OTHER PUBLICATIONS

International Search Report and Written Opinion dated Aug. 30, 2017 in PCT Application No. PCT/US2017/036001.
Han, Xin, et al. "CRISPR-Cas9 delivery to hard-to-transfect cells via membrane deformation." Science Advances vol. 1, No. 7, e1500454, Aug. 14, 2015.
Sharei, Armon, et al. "Cell Squeezing as a Robust, Microfluidic Intracellular Delivery Platform." Journal of Visualized Experiments, JoVE, vol. 81, e50980, Nov. 2013.
Williams, A. R., et al. "Filtroporation: A Simple, Reliable Technique for Transfection and Macromolecular Loading of Cells in Suspension." Biotechnology and Bioengineering, vol. 65, No. 3, pp. 341-346, Nov. 1999.
Chuck, Alice S., et al. "Consistent and High Rates of Gene Transfer Can Be Obtained Using Flow-Through Transduction over a Wide Range of Retroviral Titers" Human Gene Therapy, vol. 7, No. 6, pp. 743-750, Apr. 10, 1996.
Chuck, Alice Siw Ying. "Directed Retroviral Motion as a Means of Enhancing Gene Transfer for Gene Therapy" (Doctoral Dissertation), The University of Michigan, 1995.
Chuck, Alice S., et al. "Membrane Adsorption Characteristics Determine the Kinetics of Flow-Through Transductions" Biotechnology and Bioengineering, vol. 51, pp. 260-270, 1996.
Cimetta, Elisa, et al. "Microfluidic-driven viral infection on cell cultures: Theoretical and experimental study" Biomicrofluidics, vol. 6. No. 2, paper 024127, Jun. 2012.
Tran, Reginald, et al. "Simplified prototyping of perfusable polystyrene microfluidics" Biomicrofluidics, vol. 8, No. 4, paper 046501, Jul. 2014.
Luni, Camilla, et al. "Stochastic Model-Assisted Development of Efficient Low-Dose Viral Transduction in Microfluidics" Biophysical Journal, vol. 104, pp. 934-942, Feb. 2013.
Tran, Reginald, et al. "Microfluidic transduction harnesses mass transport principles to enhance gene transfer efficiency" Molecular Therapy, vol. 25, No. 10, Oct. 2017.

* cited by examiner

Primary Examiner — James S Ketter
(74) Attorney, Agent, or Firm — McDermott Will & Emery LLP

(57) ABSTRACT

Systems and methods are disclosed herein for use in transducing, activating, and otherwise treating cells. Cells are introduced into an inner layer of a multi-layered stack that defines at least one flow chamber and a plurality of cell entrainment regions. Vertical flow through the stack entrains the cells in the cell entrainment regions along with genetic information introduction agents or other additives, before the cells are washed using a reverse vertical flow and are collected from the device.

23 Claims, 22 Drawing Sheets

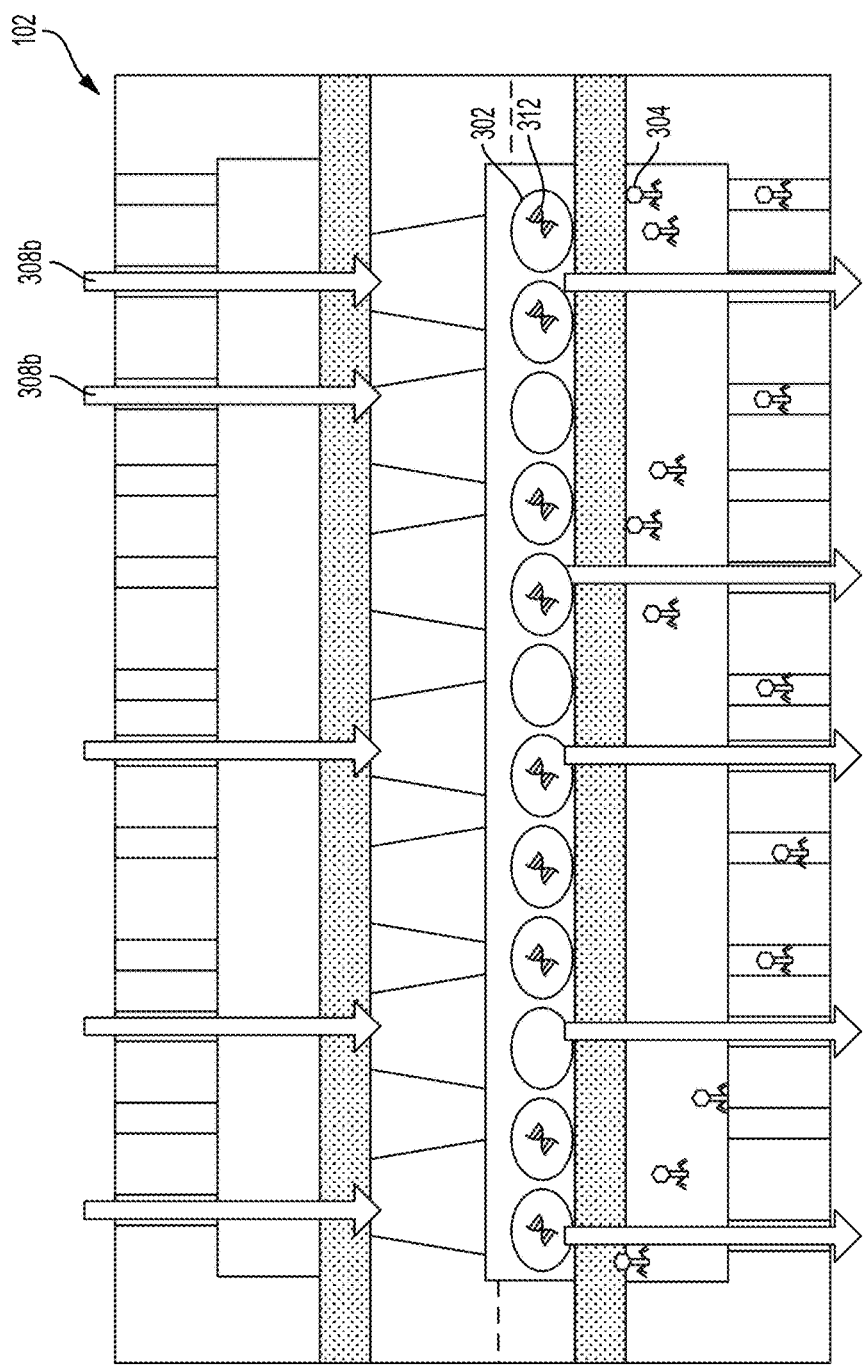

Figure X. Transduction efficiency of Jurkat cells after 30 minutes of exposure to a GFP + lentiviral vector (MOI 3, 1 million cells). Transduction efficiency was characterized by assessing total GFP+ cells/total cells.

SYSTEMS AND METHODS FOR CELL TRANSDUCTION

RELATED APPLICATIONS

The present application claims the benefit of, and priority to, U.S. Provisional Patent Application No. 62/346,031, titled "Microfluidic Viral Transduction for Chimeric Antigen Receptor T Cell Technology and Other Cell Therapies," filed on Jun. 6, 2016, and U.S. Provisional Patent Application No. 62/421,784, titled "Systems and Methods for Cell Transduction," filed on Nov. 14, 2016, both of which are hereby incorporated by reference in their entirety.

BACKGROUND

Various treatments for a variety of medical conditions involve the transfer of exogenous genetic information into cells of a patient or a cell donor. For example, CAR-T (chimeric antigen receptor T cell) technology involves taking blood samples from a patient and processing those cells in a manner that returns genetically engineered populations of T cells to the patient's body once they have been programmed to recognize specific antigens on targeted cells. Typically, genes are transferred into T cells by viral transduction with a retrovirus (e.g., lentivirus), but they can also be transfected into cells using physical methods such as electroporation or cell constriction within channels, chemical methods, or other approaches.

SUMMARY

According to one aspect of the disclosure, an apparatus includes a first substrate defining at least one first flow chamber coupled to a first fluid manifold and a second substrate defining a cell entrainment layer. The cell entrainment layer includes at least one second flow chamber and a plurality of cell entrainment cavities. Each of the cell entrainment cavities opens at one end into one of the second flow chambers. Each of the cell entrainment cavities extends through the second substrate and is sized to hold at least one cell. The cell entrainment layer includes at least one inlet to the at least one second flow chamber that is substantially within the plane of the second substrate. The cell entrainment layer includes at least one outlet from the at least one second flow chamber that is substantially within the plane of the second substrate. The apparatus includes a first membrane positioned between the first substrate and second substrate. The first membrane includes a plurality of pores that are small enough to prevent the passage of cells and large enough to allow the passage of viral particles. The apparatus includes a third substrate defining at least one third flow chamber coupled to a second fluid manifold. The apparatus includes a second membrane positioned between the second substrate and the third substrate. The second membrane includes a second plurality of pores that are small enough to prevent passage of viral particles but large enough to allow the passage of cell media.

In some implementations, the at least one first flow chamber, the at least one second flow chamber and/or the at least one third flow chamber includes a respective substantially planar flow field that couples to a corresponding manifold via a plurality of fluid connections. In some implementations the at least one first flow chamber, the at least one second flow chamber and/or the at least one third flow chamber include a plurality of flow channels. Each flow channel couples to a corresponding manifold via a single fluid connection.

In some implementations, the at least one first fluid manifold and the second fluid manifold include a vertical flow manifold. In some implementations, the at least one first fluid manifold and the second fluid manifold include a horizontal flow manifold.

In some implementations, a first end of the first fluid manifold couples to the at least one first fluid chamber defined by the first substrate, and a first end of the second fluid manifold couples to the at least one third fluid chamber defined by the third substrate. A second end of the first fluid manifold is fluidically coupled to a second end of the second fluid manifold such that fluid can circulate through the first fluid manifold, the first membrane, the plurality of cell entrainment cavities, the second membrane, the second fluid manifold and back to the first fluid manifold. In some implementations, the apparatus includes a waste channel coupled between the second end of the first fluid manifold and the second fluid manifold by a valve. The valve is configured to selectively divert fluid flow directed out of the second end of the first fluid manifold to a waste reservoir.

In some implementations, the apparatus includes a first pump configured to pump fluid into the second end of the first fluid manifold. In some implementations, the apparatus includes a second pump configured to pump fluid into the second end of the second fluid manifold, and wherein the second pump is the same pump as the first pump or different than the first pump.

In some implementations, the first substrate includes an outlet coupled to a distal end of the at least one first fluid chamber.

In some implementations, the cell entrainment cavities have a greater density towards a distal end of the at least one second fluid chambers than towards a proximal end of the at least one second fluid chambers.

According to another aspect of the disclosure, a method of cell transduction includes introducing cells into at least one first flow chamber and introducing genetic information introduction agents into the first flow chamber. The method includes flowing a first fluid in a first direction substantially normal to the at least one first flow chamber and through a plurality of cell entrainment cavities distributed along the at least one first flow chamber having proximal ends open to respective first flow chambers, thereby entraining the introduced cells and genetic information introduction agents into the plurality of cell entrainment cavities for a first period of time, thereby allowing the genetic information carried by the genetic information introduction agents to be transduced into the entrained cells. The method includes preventing passage, through distal ends of the cell entrainment cavities, of the cells and the genetic information introduction agents. The method includes reversing the direction of flow of the first fluid for a second period of time, thereby releasing the cells from the cell entrainment cavities and washing the genetic information introduction agents away from the cells. The method includes flowing the released cells out of the at least one first flow chamber for collection.

In some implementations, the method includes flowing the first fluid through a first membrane having pores sized to prevent passage of the cells but large enough to allow passage of the genetic information introduction agents. In some implementations, the method includes flowing the first fluid through the distal end of the cell entrainment cavities through a second membrane having pores sized large enough to allow passage of first fluid and small enough to prevent passage of the genetic information introduction agents through the second membrane. In some implementations, the method includes creating a circulating flow in which fluid flowing through the second membrane is redirected back through the first membrane in the first direction.

In some implementations, the method includes introducing the cells and the genetic information introduction agents into the first flow field substantially simultaneously. In some implementations, the method includes introducing the cells into the first flow field prior to the introduction of the genetic information introduction agents into the first flow field.

According to another aspect of the disclosure, an apparatus includes a first substrate defining at least one first flow chamber coupled to a first fluid manifold. The apparatus includes a second substrate defining at least one second flow chamber. The second flow chamber includes a first membrane positioned between the first substrate and the second substrate. The first membrane includes a plurality of pores that are small enough to prevent the passage of cells and large enough to allow the passage of a virus. The apparatus includes a third substrate defining a third flow chamber and coupled to a second fluid manifold. The apparatus includes a second membrane positioned between the second substrate and the third substrate. The second membrane includes a second plurality of pores that are small enough to prevent the passage of viral particles but large enough to allow the passage of cell media. The apparatus includes a means for entraining cells within the at least one second flow chamber as a result of a flow of fluid across the first and second membranes.

In some implementations, the means for entraining includes the second membrane. In some implementations, the second membrane includes one of a patterned membrane and an unpatterned membrane.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 3A-3E show various stages of the execution of the method shown in FIG. 2 using a cell transduction stack suitable for use in the cell transduction systems shown in FIGS. 1A and 1B;

DESCRIPTION OF CERTAIN ILLUSTRATIVE IMPLEMENTATIONS

Figure 1A:
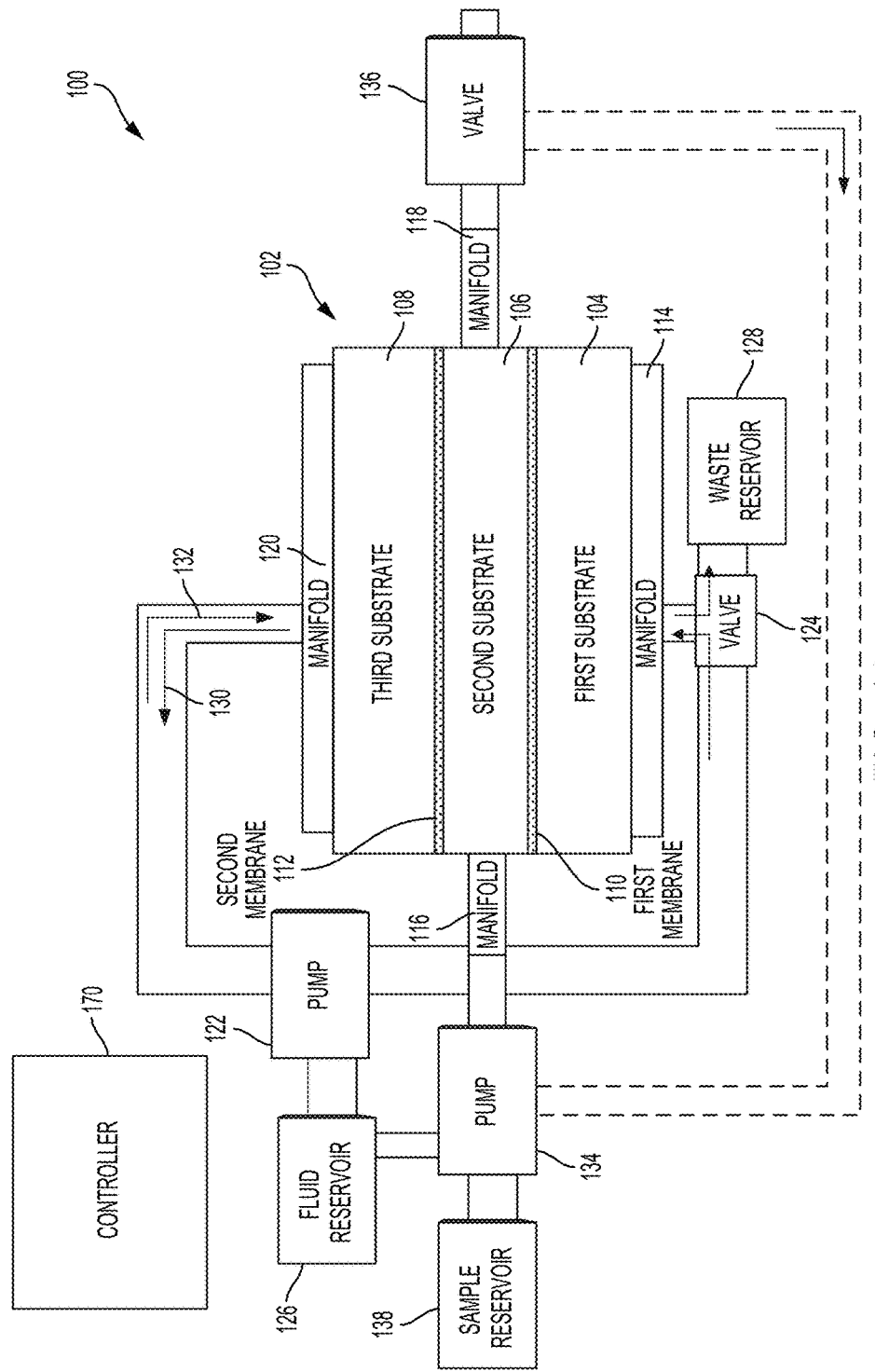
FIG. 1A is a block diagram of an example cell transduction system.

The various concepts introduced above and discussed in greater detail below may be implemented in any of numerous ways, as the described concepts are not limited to any particular manner of implementation. Examples of specific implementations and applications are provided primarily for illustrative purposes.

Systems and methods are disclosed herein for use in the transduction process involved in CAR-T (chimeric antigen receptor T-cell) and other cell modification or stimulation regimens. Other example uses of the technology disclosed include protein and virus production, cell expansion, reprogramming of stem cells, silencing of particular genes for treatment of genetic diseases, activation of T-cells, or siRNA delivery. Other uses of the systems and methods could be implemented without departing from the scope of this disclosure.

The devices discussed herein generally include three layers, separated from one another by membranes. Each layer defines at least one flow chamber. As used herein, a "flow chamber" refers to any conduit for carrying fluid across a layer in the device. Flow chambers can generally be classified as either flow channels or flow fields. As used herein, a "flow field" refers to a wider flow chamber which couples to a manifold via multiple fluid connections. In contrast, as used herein, a "flow channel" refers to a narrower flow chamber that couples to a manifold via a single fluid connection. Accordingly, in some implementations, each layer defines one or more flow fields. In some other implementations, each layer defines multiple flow channels. In some implementations, at least one layer includes one or more flow fields and one or more other layers includes multiple flow channels.

The layers of the devices discussed herein are configured to allow for a reversible vertical flow across the flow chambers defined in each layer in a direction substantially normal to the planes of the layers, themselves, as well as for horizontal flow at least through the central layer. The central layer defines cell entrainment regions in which cells and genetic information introduction agents or other chemical or biologic additives can be entrained to cause the genetic information carried by the genetic introduction agents (or the additives) to be introduced into (or otherwise interact with) the entrained cells. Such additional additives may include antibodies, cytokines, small molecules, proteins, or any other agent that might interact with the entrained cells. The horizontal flow through the central layer is used to introduce cells and genetic information introduction agents or other additives into the central layer, distribute the cells and genetic information introduction agents or additives amongst the cell entrainment regions, and then remove cells from the central layer after treatment. The vertical flow across the layers is used to entrain the cells and genetic information introduction agents or additives into the cell entrainment regions. The vertical flow can then be reversed to release the cells from the cell entrainment regions and then wash away excess genetic introduction agents or additives.

In various embodiments, fluid flows are introduced into the flow chambers of the three layers of the device through either external fluid manifolds or integrated fluid manifolds. External fluid manifolds are formed in separate components and are fluidically coupled to the flow chambers via fluid passageways defined into the layers. Integrated fluid manifolds are formed directly into the material that makes up a particular layer. In some implementations, the fluid manifolds introducing fluid into each of the layers are horizontal fluid manifolds. In some implementations, the fluid manifolds introducing fluid into the outer two layers are vertical fluid manifolds.

In some implementations, fluids may be introduced into a given layer via an external manifold and removed through an integrated manifold, or vice versa. In some implementations, at one of both ends of a given layer, an external manifold may couple to an integrated manifold.

The two membranes in the device are selected to control the passage of fluid and biologic material between the layers of the device. The membranes can be generally impermeable, except through specifically defined pores through the membrane. The pores of one membrane are sized to be large enough to allow passage of fluid, such as cell media, but small enough to prevent passage of genetic information introduction agents or other additives introduced into the system. The pores of the other membrane are larger, allowing the passage of genetic information introduction agents or other additives introduced into the system, but are still small enough to prevent the passage of cells. In some implementations, the pores of both membranes may be large enough to allow genetic introduction agents or other additives to pass. In such implementations, genetic introduction agents or other additives recirculate through the device with the vertical flow.

FIG. 1A is a block diagram of an example cell transduction system 100. The system includes a transduction stack 102 and associated fluidics that control the flow of fluid into and out of the transduction stack 102.

The transduction stack 102 includes a first substrate 104, a second substrate 106, and a third substrate 108. The first substrate 104 is separated from the second substrate 106 by a first membrane 110, and the second substrate 106 is separated from the third substrate 108 by a second membrane 112.

In the example cell transduction system 100, the first substrate 104 defines a first flow field which extends substantially in a plane that is parallel to the plane of the first substrate 104. The first substrate 104 further defines a plurality of fluid passageways passing through a first side of the first substrate 104 opposite the first membrane 110. The fluid passageways extend substantially normal to the planes of the first substrate 104 and the first flow field. The fluid passageways are distributed substantially evenly across the first side of the first substrate and fluidically couple the first flow field to a first external fluid manifold 114. The first external fluid manifold 114 introduces fluid into the cell transduction stack 102 through a two dimensional array of fluid passages, allowing a fluid introduced by the cell transduction system 100 to be introduced in a substantially even manner across the first flow field in a direction normal to the planes of the first substrate 104 and the first flow field, yielding, in some implementations, a substantially uniform flow of fluid across the flow field.

The second substrate 106 defines a second flow field. The second flow field is likewise substantially planar and extends in a plane substantially parallel to the plane of the second substrate 106. The second substrate 106 defines a plurality of inlets along a first edge of the second substrate, which fluidically couple the second flow field to outlets of a second external fluid manifold 116. The second external fluid manifold distributes a second fluid along the edge of the second substrate such that second fluid enters the second flow field substantially evenly along a corresponding edge of the second flow field. The second fluid is introduced in a direction that is normal to the direction of the flow of the first fluid discussed above. That is, the second fluid is flowed within the plane of the second flow field. The second substrate further defines a plurality of outlets distributed along a second edge of the second substrate 106, opposite the first edge. The outlets fluidically couple the second flow field to a third external fluid manifold 118, which carries fluid out of the second flow field.

In some implementations, the second substrate 106 defines an array of cell entrainment cavities. The cell entrainment cavities can be formed from holes penetrating the second substrate 106 in a direction substantially normal to the plane of the second substrate 106. The holes are sufficiently wide at the end proximate to the second flow field (the "proximate end") and deep enough to hold at least one cell. In some implementations, the holes are each sized and shaped to hold a single cell. In some implementations, the holes are sized and shaped to hold multiple cells ranging from one cell to thousands or even about a million cells. For example, the holes may be generally circular, hexagonal, octagonal, rectangular, elliptical, or have any other suitable shape. In some implementations, the proximate end may have a diameter of between about 0.01 mm to about 1.0 mm. In some implementations, the proximate end may have a diameter of between 0.1 mm and 1.0 mm. In some implementations, the proximate end may have a diameter of between about 0.50 and about 0.80 mm. The cell entrainment cavities can have depths ranging from about 0.01 mm to about 2.0 mm. In some implementations, the cell entrainment cavities are between about 0.1 mm and about 0.5 mm deep. In some implementations, the walls of the cell entrainment cavities are vertical (i.e., normal to the plane of the second substrate 106). In some other implementations, the walls of the cell entrainment cavities are sloped, such that the cell entrainment cavities narrow as they approach their distal end, adjacent the second membrane 112. The slope of the walls can range from about 45 degrees up to about 90 degrees. In some implementations, the walls can have a slope of between about 60 degrees to about 80 degrees. The cell entrainment cavities can be rather tightly packed across the second substrate 106. In some implementations, the cavities can be arranged in a staggered fashion to maximize packing density. In some other implementations, the cavities can be arranged in a rectangular, hexagonal, or other geometric array. The space between cell entrainment cavities in any direction can be less than the diameter of the proximal end of the holes forming the cell entrainment cavities. In various implementations, the second substrate may define between about 1,000 cavities and about 10,000,000 cell entrainment cavities. In some implementations, the cavities are regularly spaced along the length of the flow field. In some implementations, the cavities are irregularly spaced. For example, for implementations including flow channels, cavities can be more densely packed toward the distal end of the flow channels to ensure cells are likely to be entrained before reaching the end of the channel. For some implementations including flow fields, the density of cavities along the central axis of the flow field may be higher than towards the edges as cells are likely to migrate towards the center of the flow fields. In addition, or in the alternative, in some flow field implementations, the density of cavities may be greater at the distal end of the flow field than at the proximal end of the flow field. In some implementations, the cavities may be positioned such that a substantially equal number of cells are entrained in each cavities. The width of the cavities may be designed to house at least one cell, but may also be keyed to the width of the flow chamber to enable multiple cells in an individual cavity or to promote ease of manufacturing processes such as alignment.

In some other implementations, the second substrate 106 does not define cell entrainment cavities, and instead holds a porous gel or mesh adjacent to the second flow field, in which cells can become entrained. The porous gel or mesh may be impregnated with chemical factors, such as cytokines, and/or genetic information introduction agents, such as viruses, viral particles, plasmids, plasmid vectors, CRISPR complexes or any other means for introducing genetic information into a cell including agents of vector introduction such as lipofectamine. The gel or mesh is permeable to fluid flowing through the second flow field, and contains cavities within it which can entrain cells.

The third substrate 108 defines a third flow field and a second plurality of fluid passageways Like the first plurality of fluid passageways defined through the first substrate 104, the second plurality of fluid passageways extend through third substrate 108 in a two-dimension array in a direction substantially normal to the plane of the third substrate 108. The second plurality of fluid passageways fluidically couple the third flow field to a fourth external fluid manifold 120.

While shown in FIG. 1A as being coupled to external fluid manifolds, in some implementations, one or more, and in some cases, all of the substrates 104, 106, and 108 include integrated fluid manifolds. Example integrated manifolds are shown in FIGS. 7C and 7D.

Each of the first, second, and third substrates 104, 106, and 108 can be made of polystyrene, polycarbonate, polyimide, polyetherimide (PEI), polysulfone, polyethersulfone, acrylic, or cyclic olefin copolymer (COC), biodegradable polyesters, such as polycaprolactone (PCL), soft elastomers such as polyglycerol sebacate (PGS), other thermoplastics or other structural materials. The substrates may alternatively be made of polydimethylsiloxane (PDMS), poly(N-isopropylacrylamide), polyurethane (PU), fluorinated ethylene propylene (FEP), or a fluoropolymer elastomer. In some implementations, one or more of the first, second, and third substrates 104, 106, and 108 can be formed from glass, a ceramic, or a semiconductor, such as Silicon (Si). The substrates 104, 106, and 108 can range from about 0.5 mm to about 4 mm thick. In some implementations, the substrates are between about 0.5 and about 2.0 mm thick. The combined set of flow chamber(s) for a given layer, including one or more parallel flow fields or flow channels, can be generally rectangular or square shaped with dimensions running from about 5 mm wide by about 5 mm long by about 0.1 mm deep to about 20 cm long by about 20 cm wide by about 2 mm deep. In some implementations the length:width ratio of the combined set of flow chambers in a layer is about 1:1. In some implementations, one or more of the flow chambers have a circular, oval, hexagonal, or other geometric or irregular shape. In some implementations, instead of including one or wider flow fields in each layer of the transduction stack 102, or ore more of the layers can include a greater number of parallel flow channels. In some implementations, multiple cell transduction stacks 102 can be connected to the fluidics in parallel to allow for the processing of more cells at a time.

The first membrane 110 separates the first flow field defined by the first substrate 104 from second flow field defined by the second substrate 106. The membrane can be formed from a generally fluid impermeable material, such as polycarbonate, PET, or various dialysis membranes. In some implementations, the membrane material is either hydrophilic, or one or both sides of the first membrane 110 is coated with a hydrophilic material such as PVP (polyvinylpyrrolidone). Pores are formed, for example by track etching, through the first membrane 110 that are sized to be sufficiently large to allow genetic information introduction agents, such as viruses, virus particles, plasmids, CRISPR complexes, or other nucleic acid delivery agents to pass through the first membrane 110, i.e., at least about 0.1 microns and less than about 1.0 micron in diameter. In some implementations the pores are about 0.4 microns in diameter. Pores may also be formed by other techniques such as micromolding from a master mold, or by precipitation, sacrificial methods, or other techniques that produce tortuous path pores in the membranes. The first membrane 110 can have a pore density of about 15 to about 30 percent.

The second membrane 112 is similar to the first membrane 110, and separates the second substrate 106 from the third flow field. The pores of the second membrane 112, however, are smaller in diameter than the pores in the first membrane 110. The pores in the second membrane 112, for example, can be smaller than the smallest genetic information introduction agent intended to be used in the system 100. For example, the pores in the second membrane can be between about 0.001 micron and about 0.5 micron in diameter. In some implementations, the pores in the second membrane 112 are about 0.1 microns in diameter. The second membrane 112 can have a pore density of about 15 to about 30 percent. The first and second membranes 110 and 112 can be between about 8 microns and about 12 microns thick, for example about 10 microns thick.

The fluidics in the cell transduction system 100 include a vertical flow system configured to flow fluid through the transduction stack 102 bi-directionally, substantially normal to the first, second, and third substrates 104, 106, and 108. The vertical flow system includes a three-port pump 122, a three-port valve 124, the first and fourth external fluid manifolds 114 and 120, a fluid reservoir 126, a waste reservoir 128, and connecting fluid channels. The three-port pump can draw fluid, such as cell media from the fluid reservoir 126 and pump it through the transduction stack 102. The three port pump pumps the fluid through the transduction stack 102 such that the fluid enters the transduction stack 102 either through the first external fluid manifold 114 and the first substrate 104 or through the fourth external fluid manifold 120 and the third substrate 108. In one mode of operation, in which the three-port valve isolates the waste reservoir 128 from the remainder of the vertical flow system, and once a sufficient amount of fluid has been introduced into the vertical flow system from the fluid reservoir 126, the three-port pump 122 can isolate the fluid reservoir 126 from the remainder of the vertical flow system, and can recirculate the fluid through the transduction stack 102 in the direction shown by arrow 130 (i.e. counterclockwise in the figure). In another mode of operation, in which the three port valve fluidically couples the first external fluid manifold 114 to the waste reservoir and closes the fluid path between the first external fluid manifold 114 and the three-port pump 122, the three-port pump 122 opens the fluid path to the fluid reservoir 126 and reverses the direction of flow through the transduction stack 102, as shown by the arrow 132. In this mode of operation, fluid from the fluid reservoir 126 flows into the transduction stack 102 from the fourth external fluid manifold 120, out through the first external fluid manifold 114, into the waste reservoir 128 through the three-port valve.

The fluidics of the cell transduction system 100 also includes a horizontal flow system. The horizontal flow system is configured to introduce cells (and in some implementations genetic information introduction agents) into the second flow field defined in the second substrate 106 of the transduction stack 102. The horizontal flow system introduces the cells in a direction that is within the plane of the second flow field. The horizontal flow system includes a pump 134, an outlet valve 136, a sample reservoir 138, the second and third external fluid manifolds 116 and 118, and connecting fluid channels.

In some implementations, the pump 134 is a three-port pump. In such implementations, a first port couples to the sample reservoir 138, a second port couples to the fluid reservoir 126, and a third port couples to the second external fluid manifold. The pump 134, in such implementations can either pump fluid from the sample reservoir, including, for example cells and genetic information introduction agents suspended in cell media, or fluid form the fluid reservoir 126 into the transduction stack 102 through the second external fluid manifold 116.

In implementations in which the pump 134 is a four-port-pump, the fourth port of the pump couples to the outlet valve 136. In such implementations, fluid can be recirculated through the second flow field, out through the third external fluid manifold 118, through the outlet valve 136, and back to the pump 134. Such implementations can be useful if an insufficient number of cells or number of genetic information introduction agents are successfully entrained in cell entrainment cavities adjacent the second flow field as the fluid from the sample reservoir 138 makes a first pass through the second flow field. Cells or genetic information introduction agents that are not entrained can be recirculated through the second flow field in a recirculating flow to allow more of the cells and genetic information introduction agents to become entrained.

The outlet valve 136 is configured so that it also can be closed, completely preventing any flow through the outlet valve, or opened to a system output from which transduced cells can be collected.

In some other implementations, instead of being entrained in a substrate cavity, gel, or mesh, the cells can be entrained directly up against the second membrane 112. In some implementations, the second membrane 112 may be patterned to form a relief with raised regions and lower regions, to enhance the ability of the membrane to entrain cells. The lower regions can have dimensions on the order of 0.01 microns to 0.8 microns. One or more of the cells can be entrained within these lower regions, depending on their relative sizes. In some implementations, an unpatterned second membrane can serve as a means for entraining cells.

Figure 1B:
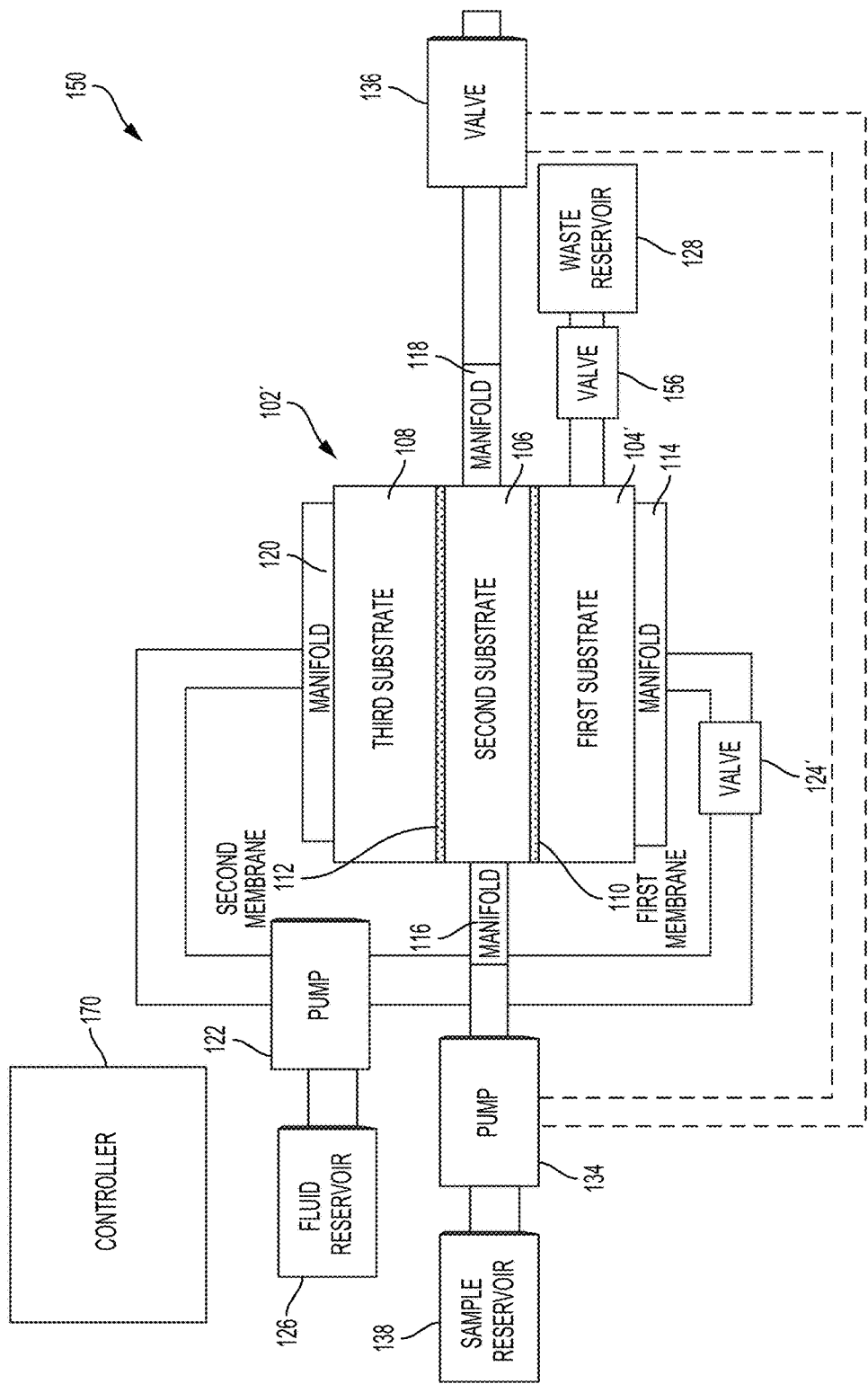
FIG. 1B shows a second example cell transduction system.

FIG. 1B shows a second example cell transduction system 150. The cell transduction system 150 is substantially similar to the cell transduction system 100 with the following differences. First, in addition to the first plurality of fluid passageways, the first substrate 104' of the cell transduction system 150 includes one or more outlets along one edge of the first flow field, allowing an alternate path for fluid to escape the first flow field. The waste reservoir 128 of the cell transduction system 150 is coupled to the one or more outlets instead to the valve 124. In some implementations in which the first substrate 104' defines multiple outlets along its edge, the cell transduction system 150 may include a fifth external fluid manifold between the first substrate 104' and the waste reservoir to combine the outflows from the first substrate 104'. The cell transduction system 150 can include a second valve 152 between the first substrate 104' and the waste reservoir 128 to gate the flow of fluid therebetween. Given the different location of the waste reservoir 128, instead of including a three-port valve between the pump 134 and the first external fluid manifold, the cell transduction system 150 uses a two-port valve 124', which either allows flow through the valve, or prevents its flow.

Each of the cell transduction systems 100 and 150 can also include a controller 170 configured to control the pumps and valves included therein to carry out the functionality and methods described herein. For example, the controller 170 can be a special purpose or general purpose processor executing computer executable instructions configured to carry out the herein disclosed methods, either automatically, or in response to user interactions.

The differences in operation between the cell transduction system 100 shown in FIG. 1A and the cell transduction system 150 shown in FIG. 1B is described further below in relation to FIGS. 3C and 3D.

Figure 1C:
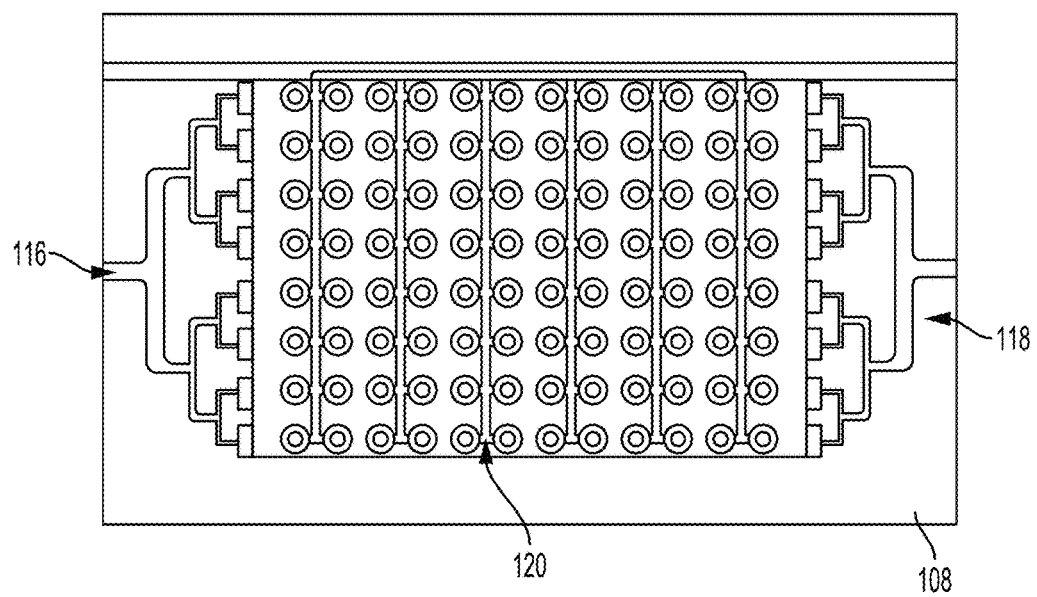
FIG. 1C shows a top view of a transduction stack suitable for use in either of the cell transduction systems shown in FIGS. 1A and 1B.

FIG. 1C shows a top view of a transduction stack 102 suitable for use in either of the cell transduction systems 100 and 150 shown in FIGS. 1A and 1B. Specifically, FIG. 1C shows examples of the second and third external fluid manifolds 116, 118 coupled to an example second substrate (not shown) and an example fourth external fluid manifold 120 coupled to an example of the third substrate 108. The example fourth external fluid manifold 120 shown in FIG. 1C distributes fluid across the top of the third substrate 108 through channels of a fourth substrate that couple to through-holes that match up to the second plurality of openings in the third substrate 108. In some implementations a similar fluid manifold can be used for the first external fluid manifold.

Figure 1D:
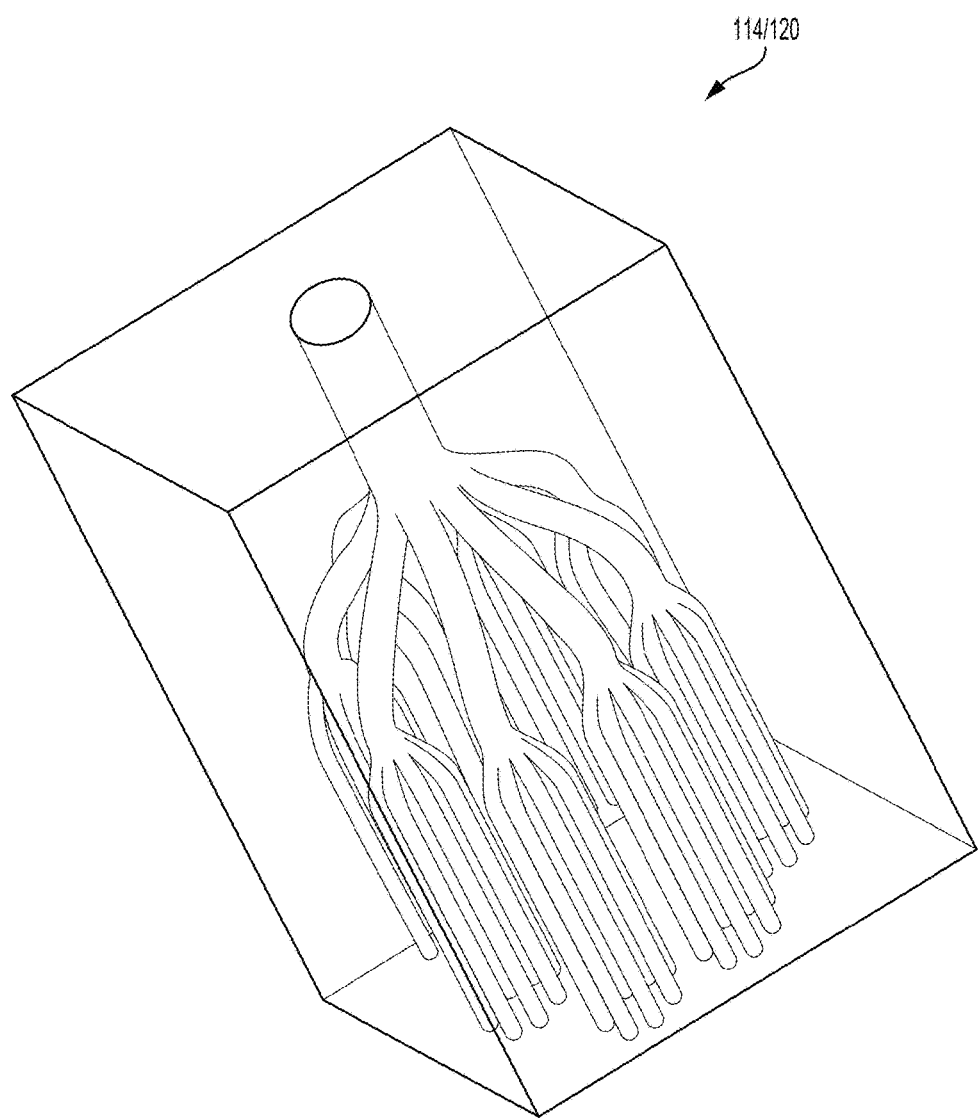
FIG. 1D shows another example manifold suitable for use as the first and fourth external fluid manifolds.

FIG. 1D shows another example manifold suitable for use as the first and fourth external fluid manifolds 114 and 120. The fluid manifold in FIG. 1D is three dimensional in nature and distributes fluid in three-dimensions (though its outputs are still arranged in two dimensions), whereas the example fourth external fluid manifold shown in FIG. 1C distributes fluid primarily only in two dimensions.

Figure 1E:
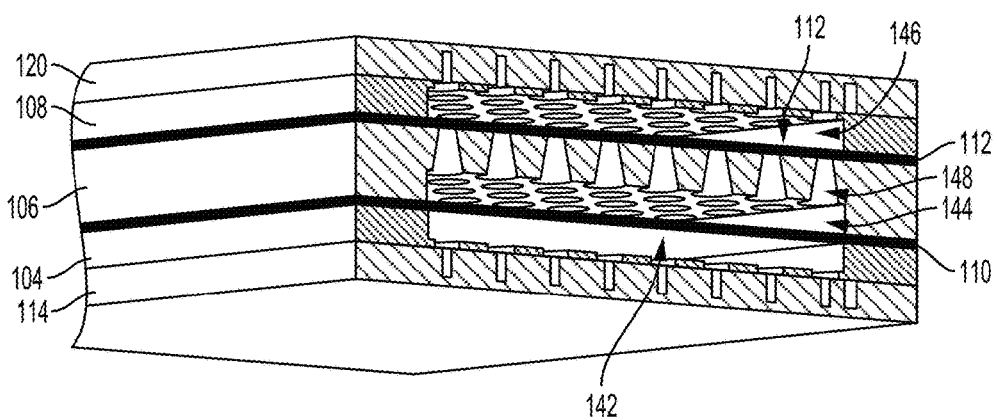
FIG. 1E shows a perspective cut-away view of an example transduction stack suitable for use in the cell transduction systems shown in FIGS. 1A and 1B.

FIG. 1E shows a perspective cut-away view of an example transduction stack 102 suitable for use in the cell transduction systems 100 and 150. Like reference numerals refer to like features in FIGS. 1A and 1B. FIG. 1E shows examples of the first flow field 142, second flow field 144, third flow field 146, and cell entrainment cavities 148, not shown in FIGS. 1A and 1B.

Figure 2:
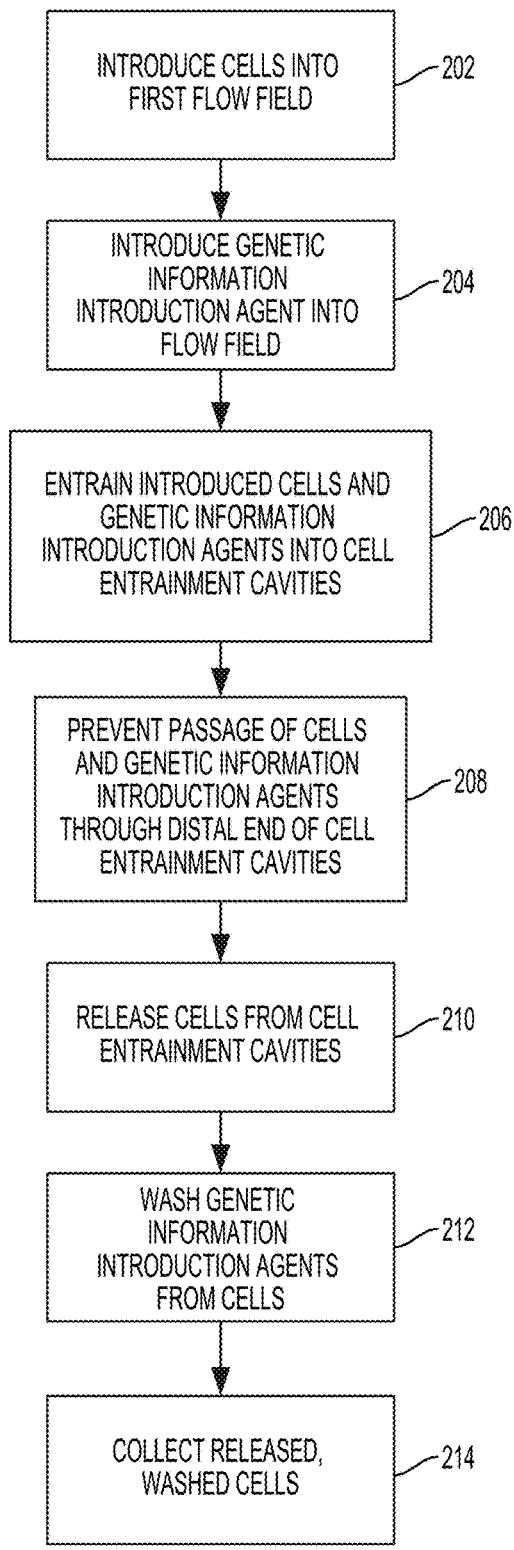
FIG. 2 shows a block diagram of an example method of transducing genetic information into cells.

FIG. 2 shows a block diagram of an example method 200 of transducing genetic information into cells. The method 200 can be implemented, for example, using the cell transduction systems 100 and 150 shown in FIGS. 1A and 1B. The method 200 includes introducing cells into a first flow field (step 202), introducing genetic information introduction agents into the first flow field (step 204), and entraining the introduced cells and the introduced genetic information introduction agents into cell entrainment cavities (step 206), while preventing passage of the cells and the genetic information introduction agents through a distal end of the cell entrainment cavities (step 208). The method 200 further includes releasing the cells from the entrainment cavities (step 210), washing the genetic information introduction agents from the released cells (step 212), and collecting the released, washed cells (step 214). Each of the above steps will be described further below with reference to FIGS. 1A and 1B and FIGS. 3A-3E, which illustrate the various steps of the method 200.

The method 200 includes introducing cells into a first flow field (step 202). The first flow field referenced in the method 200 can be, for example, the second flow field 144 defined by the second substrate 106 of the cell transduction systems 100 and 150. The cells, in some implementations, can be T cells selected for transduction as part of a CAR-T cell immunotherapy regimen. Other suitable cell types include epithelial cells, endothelial cells, cancer cells, hematopoietic stem cells, mesenchymal stromal cells, induced pluripotent stem cells, embryonic stem cells for use in gene editing, ex-vivo gene therapy, and stem cell reprogramming applications. The cells can be introduced while suspended in a fluid, such as cell media. The media containing the cells can be pumped through the horizontal flow system discussed above by the pump 134. The cells can be pumped from the sample reservoir 138 through the second external fluid manifold 116, and into the second flow field 144. In some implementations, the valve 136 is set to direct fluid that exits the second flow field back to the pump 134 to create a recirculating flow so that a sufficient number of cells can be entrained within the second substrate 106 (as discussed further below in relation to step 206). In some implementations, cell media, absent any cells, is first pumped from the fluid reservoir 126 through the horizontal flow system before the cells are introduced to prime the transduction stack 102.

Genetic information introduction agents, such as viruses, viral vectors, lipid nanoparticles, plasmids, CRISPR complexes, or other nucleic acid vectors are also introduced into the flow field (step 204). In some implementations the genetic information introduction agents are suspended in the same fluid as the cells in the sample reservoir 138. In some implementations, the sample reservoir 138 include separate compartments, keeping cells and genetic information introduction agents separated from one another until pumped into the transduction stack, and flows from the compartments combine as they flow through the horizontal flow systems of the cell transduction systems 100 or 150. In some implementations the quantity of genetic information introduction agents in the fluid entering the second flow field 144 is sufficient to produce a vector copy number of about 1 per cell. In some implementations, the quantity of genetic information introduction agents in the fluid entering the second flow field 144 is sufficient to obtain an average vector copy number across the cell population of about 0.5 to about 2.5.

In some implementations, the cells and the genetic information introduction agents are introduced (steps 202 and 204) into the flow field simultaneously. In some other implementations, the introduction of cells (step 202) and genetic information introduction agents (step 204) are carried out serially. In some implementations, the cells are introduced into the flow field before the genetic information introduction agents. In some implementations, the genetic information introduction agents are introduced into the flow field before the cells.

The method further includes entraining the introduced cells and genetic information introduction agents into cell entrainment cavities (step 206). For example the introduced cells and genetic information introduction agents can be entrained into the cell entrainment cavities 148 shown in FIG. 1E. The introduced cells and genetic information introduction agents are entrained as a result of fluid flow driven by the vertical flow system of the cell transduction systems 100 or 150. That is, the pump 122 pumps fluid, such as cell media, through the first external fluid manifold 114, vertically through the transduction stack 102 and out through the fourth external manifold 120. In some implementations, the fluid is flowed at a rate of about 0.05 ml/minute to about 0.2 ml/minute. The flow results in a pressure gradient across the second membrane 120 of about 2 mm Hg to about 1000 mm Hg. In general, the pressure is maintained to be below about 750 mm Hg. In some implementations, the vertical flow is caused while the cells and the introduced cells, genetic information introduction agents, and/or additives are being flowed into the second flow field 144. In some other implementations, the vertical flow is caused after the cells and the introduced cells, genetic information introduction agents, and/or additives have already been introduced into the second flow field 144.

Figure 3A:
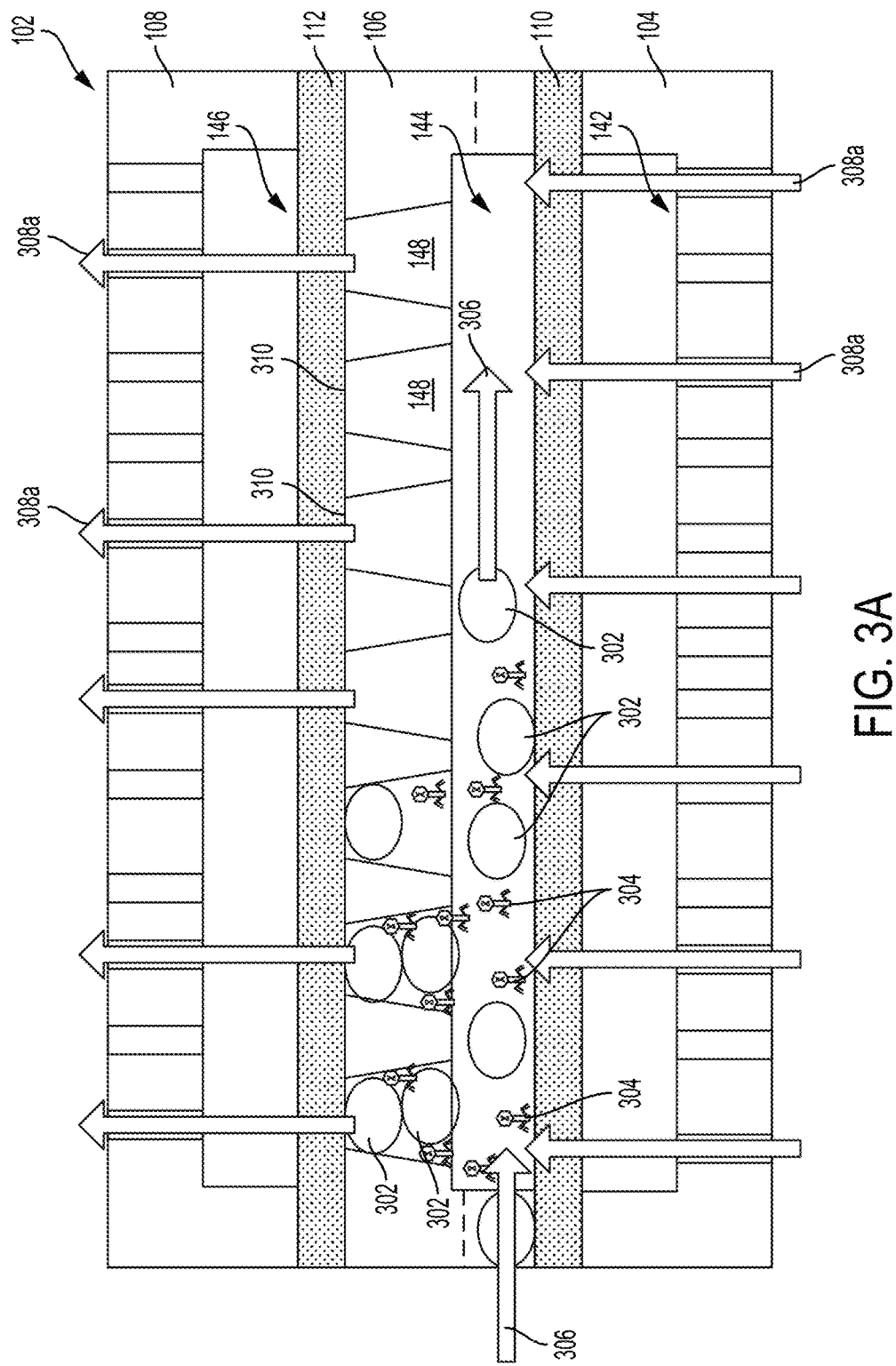

FIG. 3A shows an example of the simultaneous introduction of cells 302 and genetic information introduction agents 304 into the second flow field 144 of a cell transduction stack 102 (steps 202 and 204) via a horizontal fluid flow 306. FIG. 3A also shows the entrainment of the cells 302 and genetic information introduction agents 304 in cell entrainment cavities 148 via vertical flow 308a (step 206). While FIG. 3A shows cell entrainment cavities 148 each holding two cells, in various implementations, the cell entrainment cavities can be sized to hold between a single cell and thousands or even about a million cells.

Figure 3B:
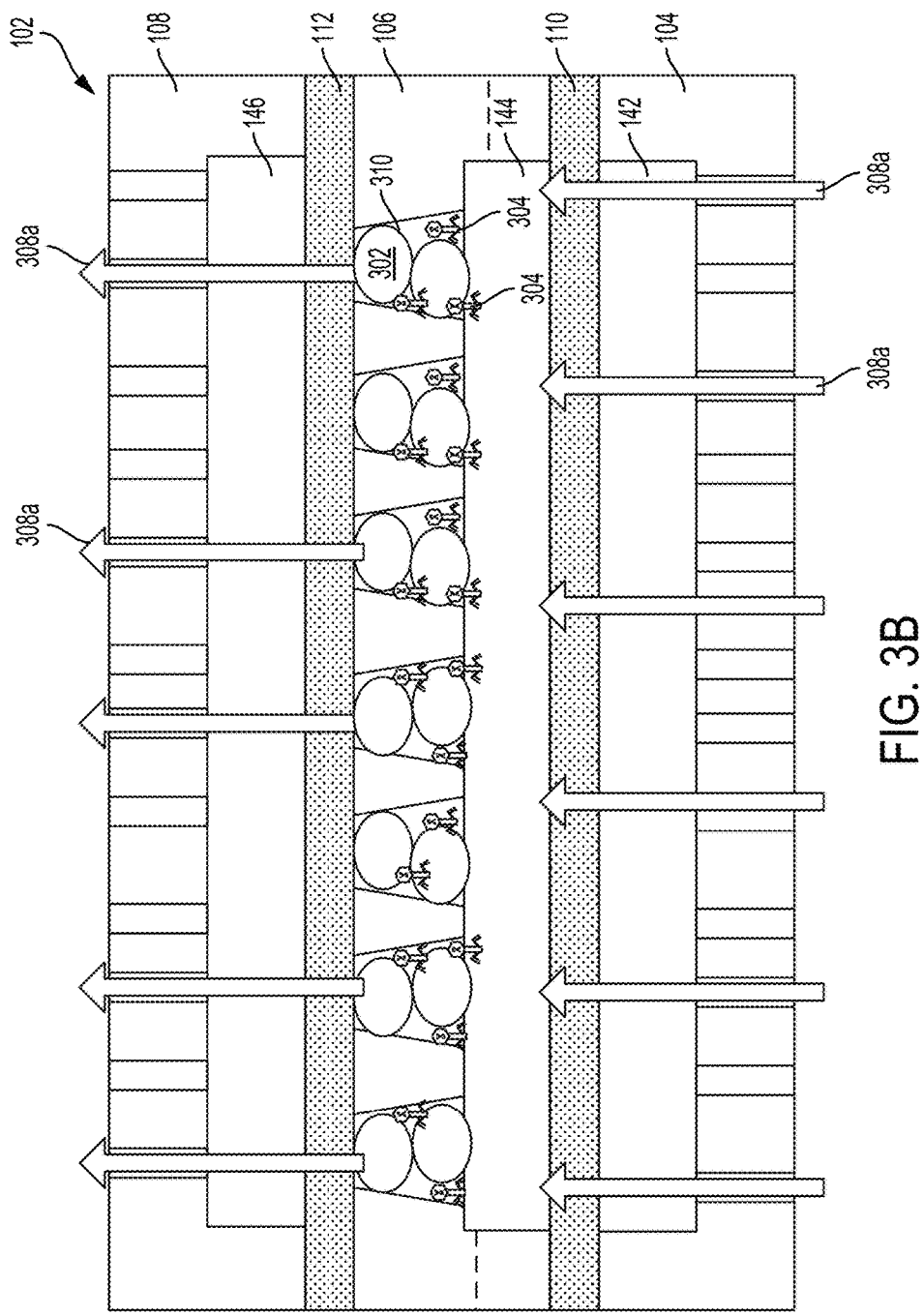
Figure 3D:
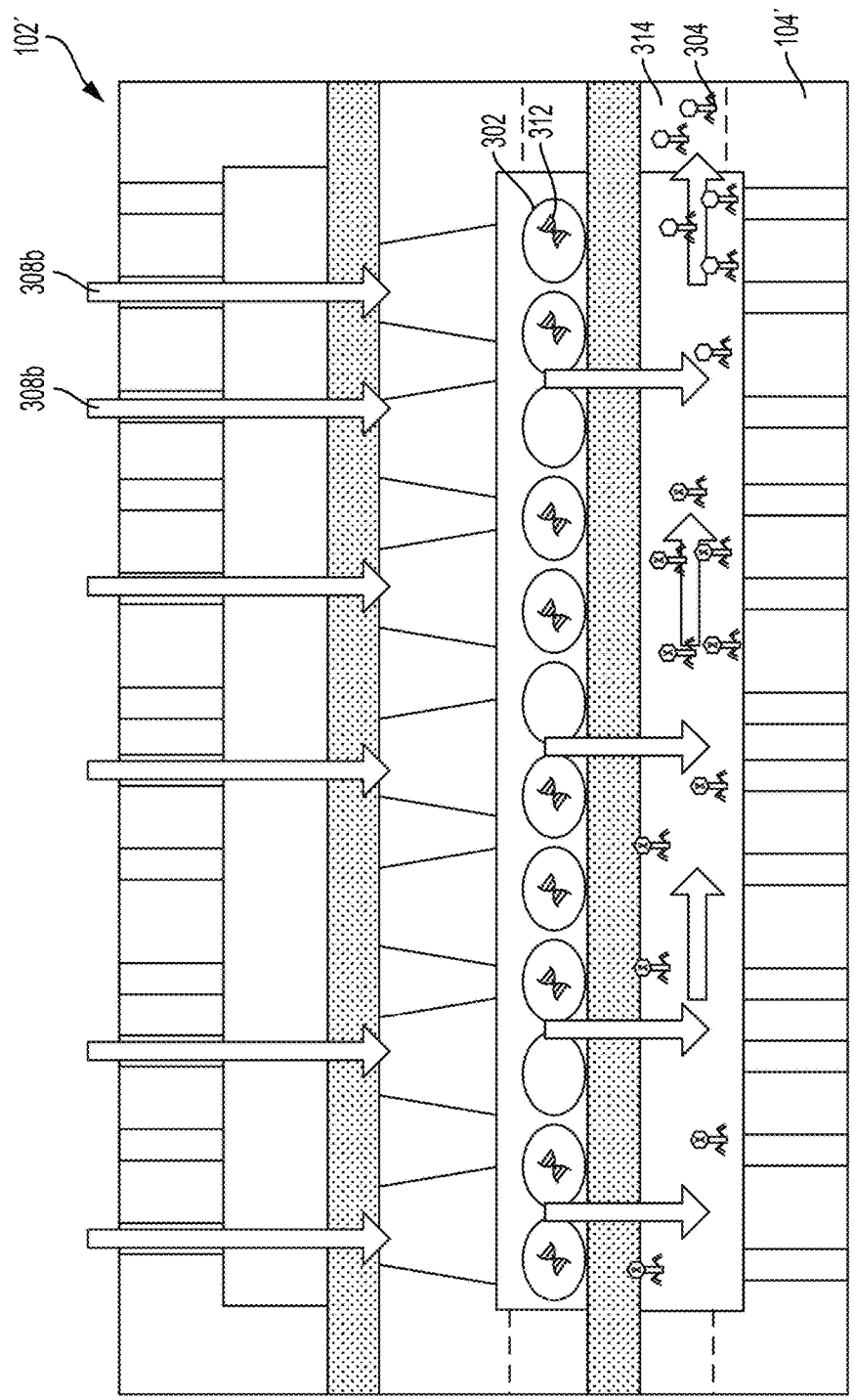

As shown in FIG. 3B, the cells 302 and genetic information introduction agents 304 remain entrained in the cell entrainment cavities for a dwell time sufficient to allow the genetic information carried by the genetic information introduction agents 304 to be introduced into the cells 302, but not so long as to endanger the viability of the cells 302. Accordingly, in some implementations, the dwell time is between about 5 minutes to about 7 hours. In some implementations, the dwell time set to be between about 10 minutes and about 2 hours. In some implementations, the dwell time is set to about 30 minutes. During this time, the vertical flow 308a through the transduction stack 102 is maintained, while preventing the passage of the cells 302 and genetic information introduction agents 304 through the distal ends 310 of the cell entrainment cavities (step 208). The passage is prevented by the second membrane 112, which has pores sufficiently large to allow the fluid of the vertical flow to pass through without building up too much pressure, but which are sufficiently small, for example between about 0.001 and about 0.5 microns in diameter, to prevent passage of the cells 302 and the smallest introduced genetic information introduction agents. During the dwell time, the horizontal flow 306 is halted and the valve 136 is closed.

Referring back to FIG. 2 and FIG. 3C and 3D, after the aforementioned dwell time, the cells 304 are released from the cell entrainment cavities 148 (step 210) and the genetic information introduction agents are washed from the cells (step 212). FIG. 3C shows an example implementation of these steps in a cell transduction stack 102 of the form shown in the cell transduction system 100 shown in FIG. 1A. FIG. 3D shows a second example implementation of these steps in a cell transduction stack 102' of the form shown in the cell transduction system 150 shown in FIG. 1B. As can be seen in FIGS. 3C and 3D, after the dwell time, many if not all of the cells become genetically modified or activated.

In both examples, the cells 304 are released (step 210) and washed (step 212) by the pump 122 reversing the direction of the vertical flow 308a to form a reverse vertical flow 308b. As such, the fluid in the vertical flow system enters the cell transduction stack 102 or 102' via the fourth external fluid manifold 120 instead of the first external fluid manifold 114. The fluid introduced in this reverse flow is drawn from the fluid reservoir 126, and is not recirculated through the vertical flow system, thereby preventing the reintroduction of the genetic information introduction agents into the transduction stack. In the example shown in FIG. 3C, recirculation is prevented by switching the three port valve 124 to redirect flow leaving the cell introduction stack into the waste reservoir 128. In the example shown in FIG. 3D, recirculation is prevented by closure of the valve 124' and opening of the second valve 156, allowing an alternate path for the fluid to flow out of the transduction stack 102 to the waste reservoir 128.

As discussed above in relation to FIG. 1A, the first membrane 110 includes pores that are large enough to allow the genetic information introduction agents 304, but not the cells 302 from passing through. Thus the reverse vertical flow 308b washes the genetic information introduction agents 304 from the cells 302 and out of the transduction stack, either through the first external fluid manifold 114 (shown in FIG. 3C) or though outlets 314 defined through an edge of the first substrate 104 (shown in FIG. 3D). The reverse vertical flow 308b can have a similar flow rate as the vertical flow 308a, e.g., between about 0.05 and 0.2 ml/minute. The cells 302 can be washed for between about 30 seconds and about 15 minutes.

Figure 3E:
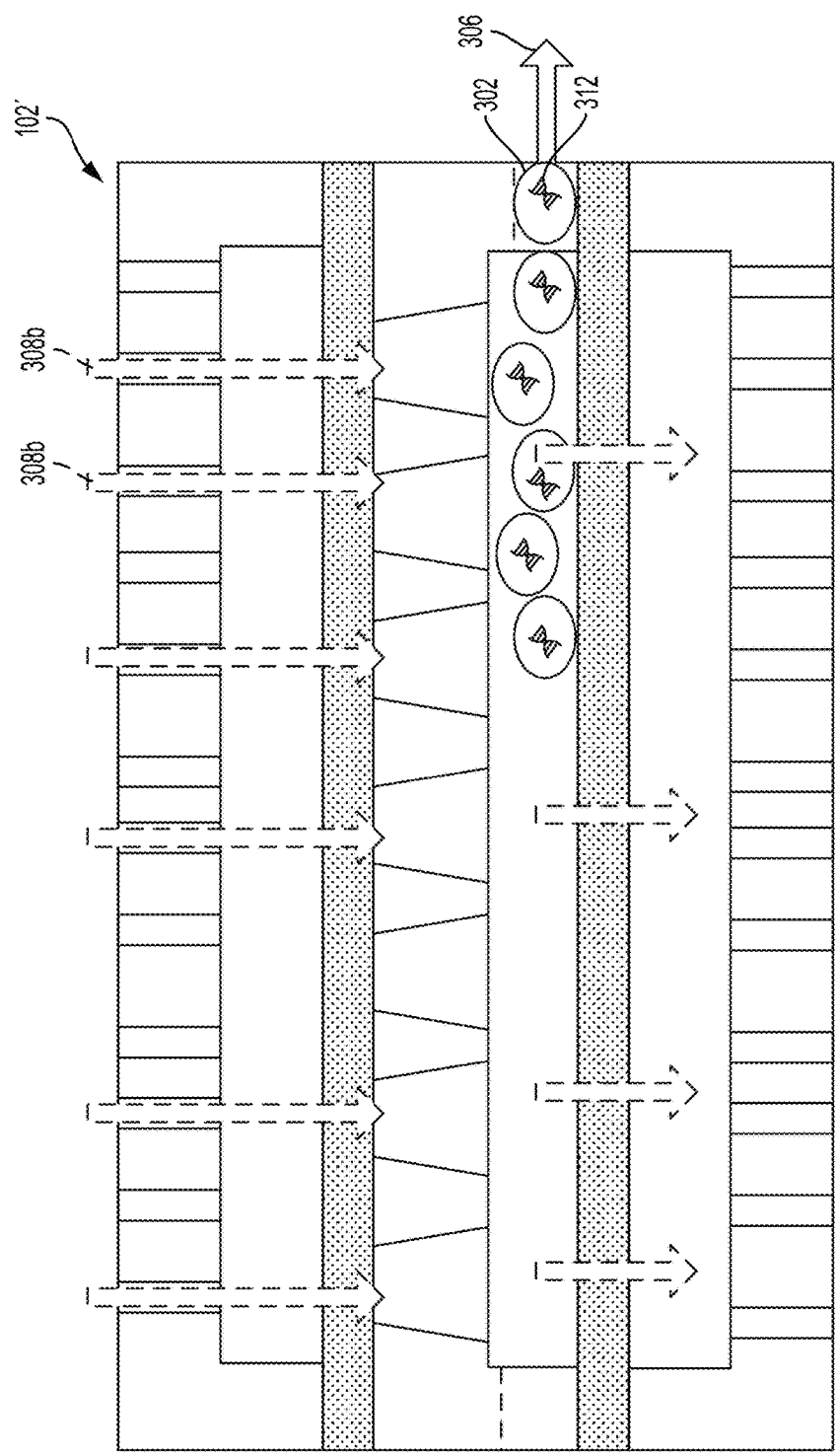

After the wash step (step 212), the cells are collected (step 214). The cells 302 are collected by the pump 134 reinitiating fluid flow through the horizontal flow system discussed in relation to FIG. 1A, forcing the cells 302 out of the transduction stack 102. In some implementations, the reverse vertical flow 308b is maintained while the cells are collected to prevent cells from getting caught in the cell entrainment cavities 148 as they exit the device. In some other implementations, the reverse fluid flow 308b is halted while the cells are collected. FIG. 3E shows an example collection of transduced cells (step 214).

In some implementations, prior to collection, the method 200 is repeated, with cells being recirculated back into the transduction stack and being introduced to another set or sets of genetic information introduction agents. In some such implementations, the additional set(s) of genetic information introduction agents carry the same additional genetic information as prior sets of genetic information introduction agents introduced into the transduction stack. In some other implementations, at least one additional set of genetic information introduction agents includes different genetic information to be introduced into the cells that prior genetic information introduction agents, thereby allowing for serial incremental introduction of genetic information into the cells.

Figure 4:
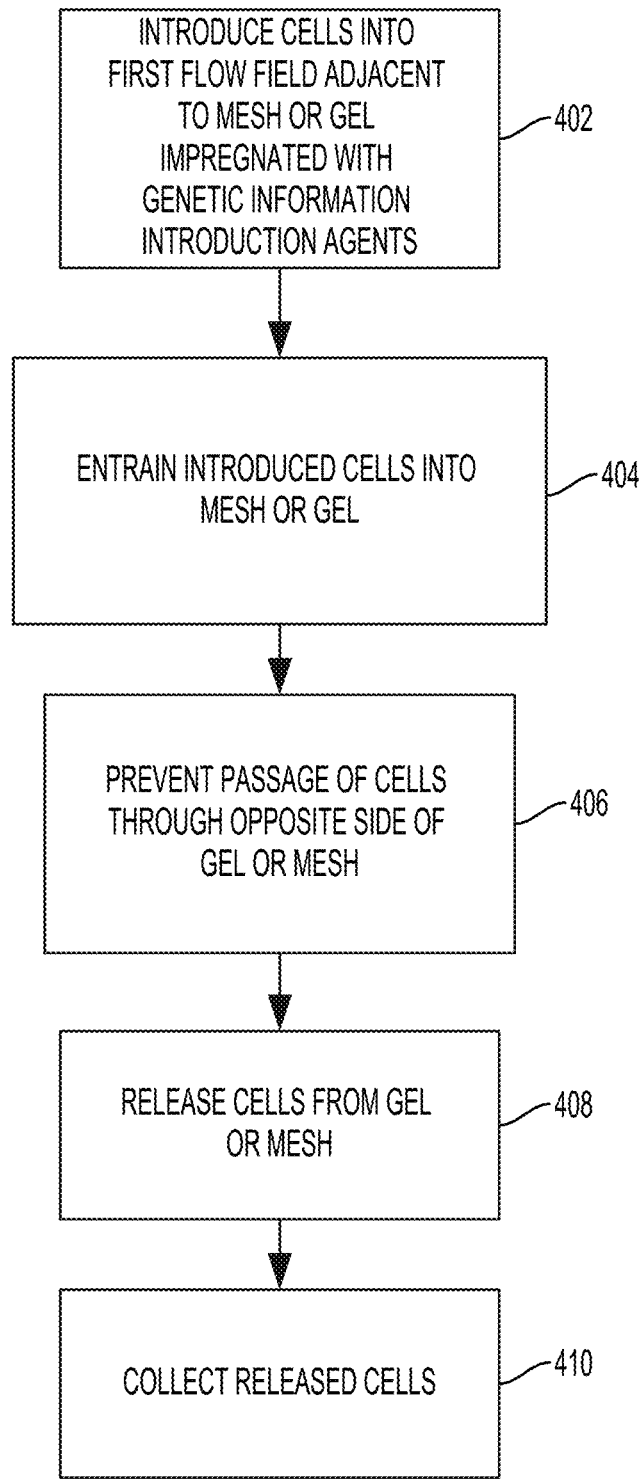
FIG. 4 shows a second example method of cell transduction using a cell transduction system similar to the cell transduction systems shown in FIGS. 1A and 1B.

FIG. 4 shows a second example method 400 of cell transduction using a cell transduction system similar to the cell transduction systems 100 and 150 shown in FIGS. 1A and 1B. In the method 400, instead of entraining cells and genetic information introduction agents into cell entrainment cavities defined in a substrate of a transduction stack, cells are flowed into the transduction stack and then are entrained in a porous mesh or gel which had been previously impregnated with genetic information introduction agents, e.g., during manufacture of the device. In implementations in which the genetic information introduction agents are introduced into the gel or mesh prior to use of the device, the transduction stack can be maintained in a suitable environment (such as a refrigeration unit, incubator, or other environment control device) to maintain the viability of the genetic information introduction agents until use. Accordingly, the method 400 includes introducing cells into a first flow field adjacent to a mesh or gel impregnated with genetic information introduction agents (step 402), entraining the introduced cells into the mesh or gel (step 404), preventing passage of cells through the opposite side of the gel or mesh (step 406), releasing the cells from the gel or mesh (step 408), and collecting the released cells (step 410). An example of this process is shown in FIGS. 5A-5D. In other implementations, the genetic information introduction agents are flowed into the transduction stack via the horizontal flow system before, after, or concurrently with the introduction of cells such that the genetic information introduction agents are entrained within the gel or mesh in intimate contact with the cells.

Figure 5A:
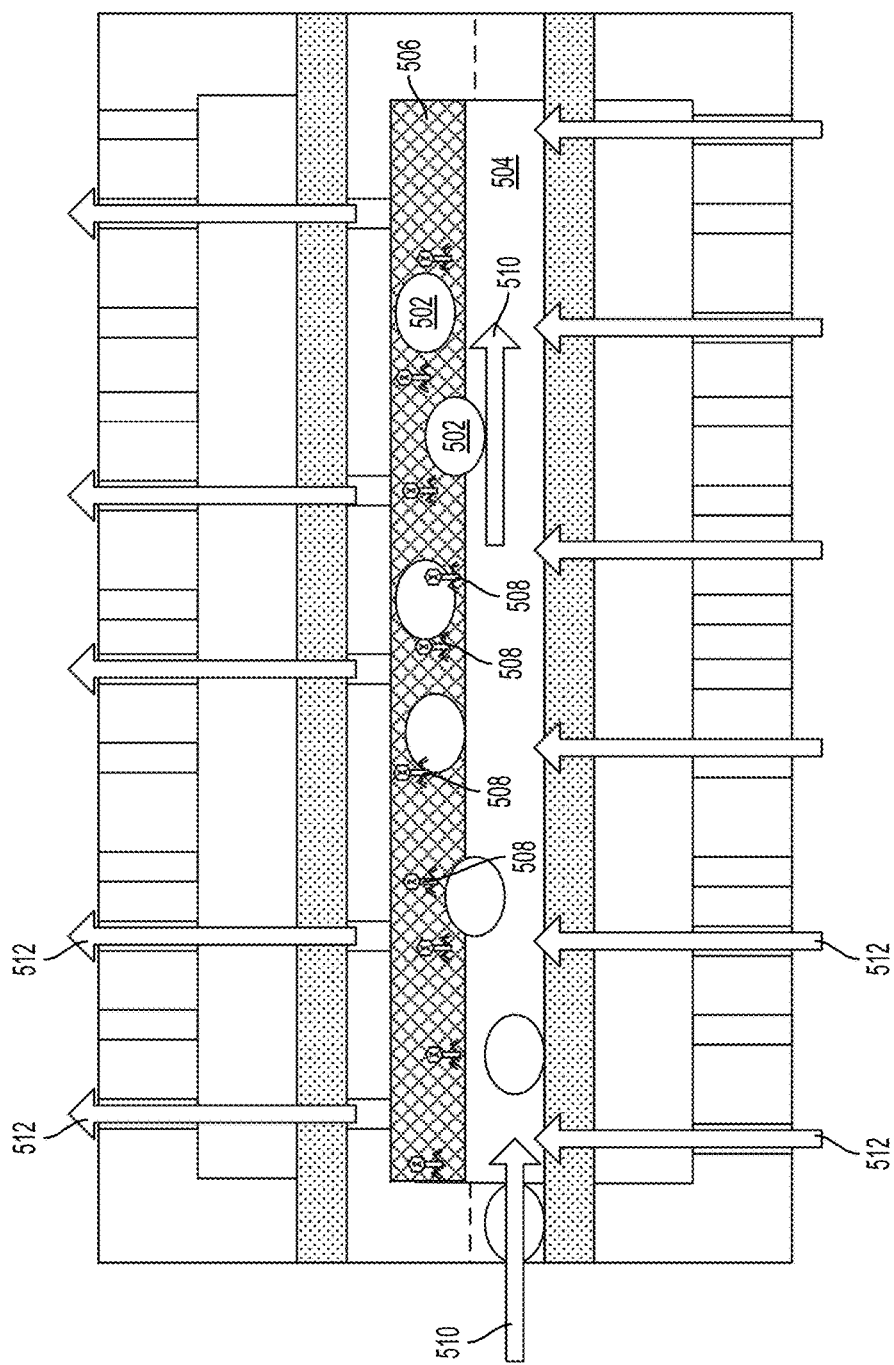
FIGS. 5A-5D show various stages of the method shown in FIG. 4 using a cell transduction stack suitable for use in the cell transduction systems shown in FIGS. 1A and 1B.

FIG. 5A shows the introduction of cells 502 into a flow field 504 adjacent a gel or mesh 506 impregnated with genetic information introduction agents 508 (step 402) and the entrainment of the cells 502 into the gel or mesh 506 (step 404). The cells 502 are introduced into the flow field (step 402) via a horizontal flow 510 generated by the pump 134 of the horizontal flow system of the cell transduction system 100 or 150, and are entrained by a vertical flow 512 generated by the pump 122 of the vertical flow system of the cell transduction system 100 or 150. The flow rates can be similar to those discussed above for the vertical flow and reverse vertical flow 308a and 308b.

Figure 5B:
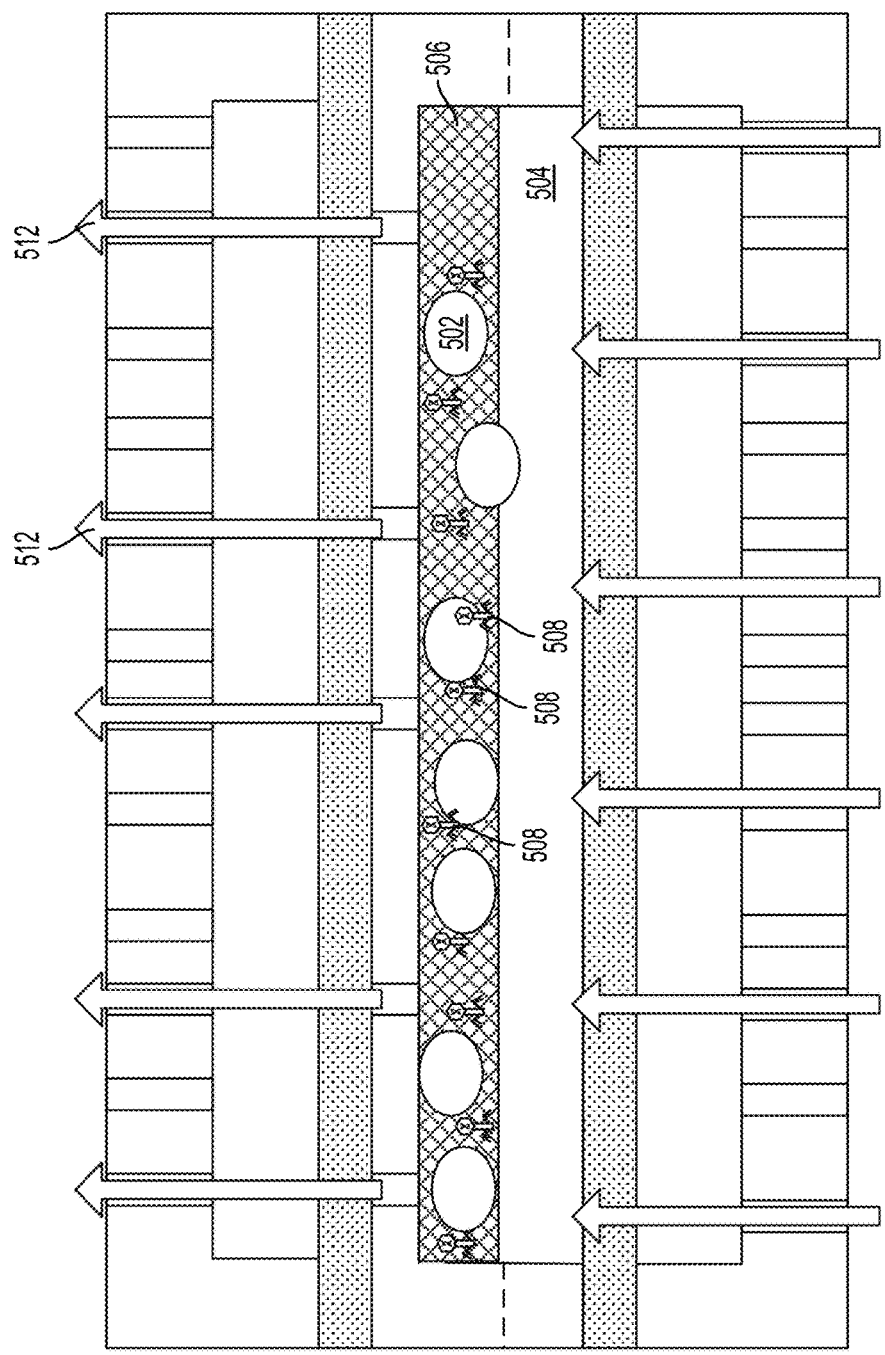

As shown in FIG. 5B, after a sufficient number of cells 502 are entrained in the mesh or gel 506, the horizontal flow 510 is halted while the vertical flow 512 is maintained for a dwell time similar in length to the dwell times discussed above with respect to FIGS. 2 and 3B, to allow time for the genetic information introduction agents to introduce their genetic information into the cells 502. The second membrane 112 prevents the cells and any genetic information introduction agents that are dislodged from the gel or mesh 506 from passing through an opposite side of the gel or mesh 506 (step 406).

Figure 5C:
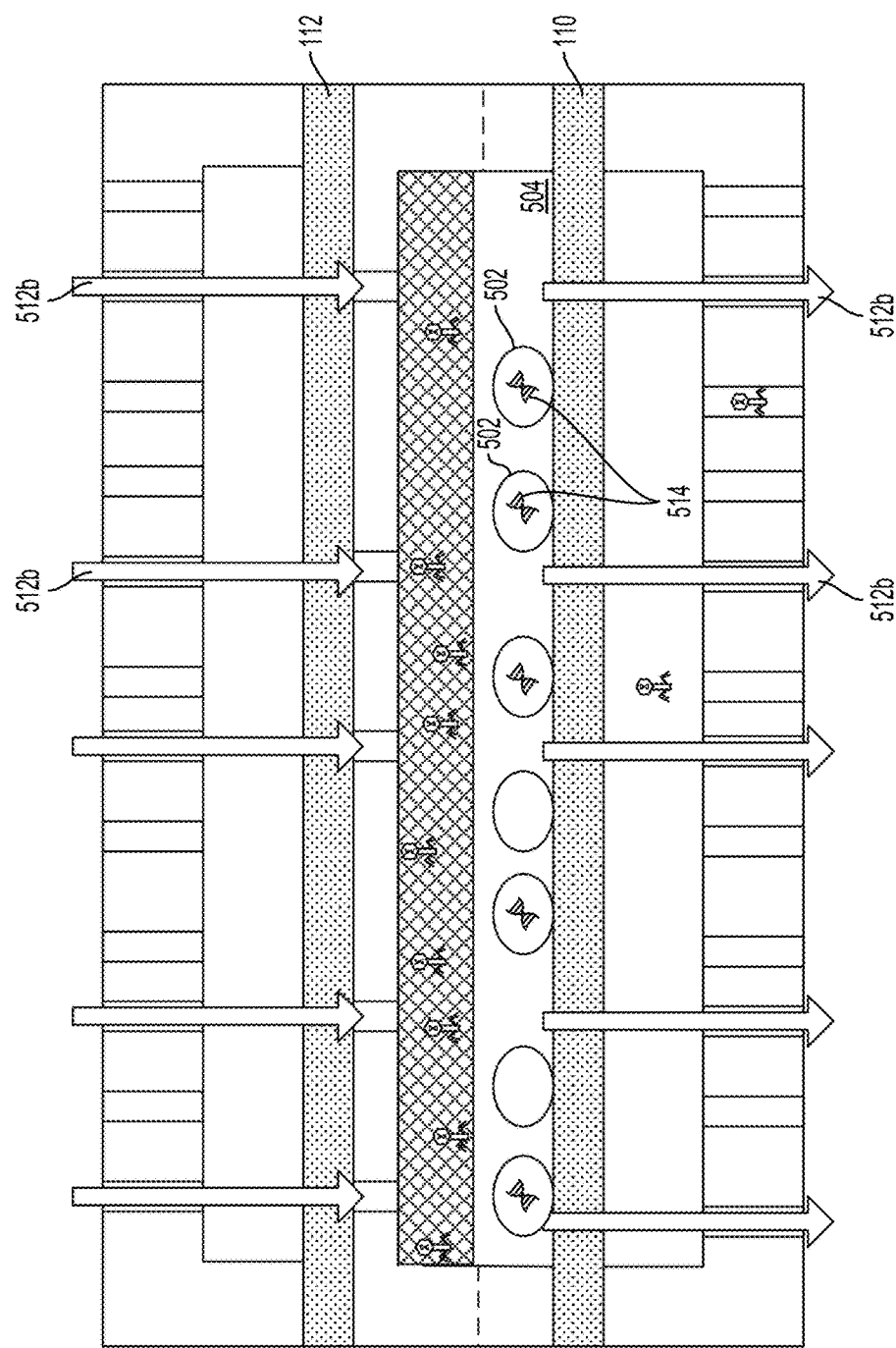
Figure 5D:
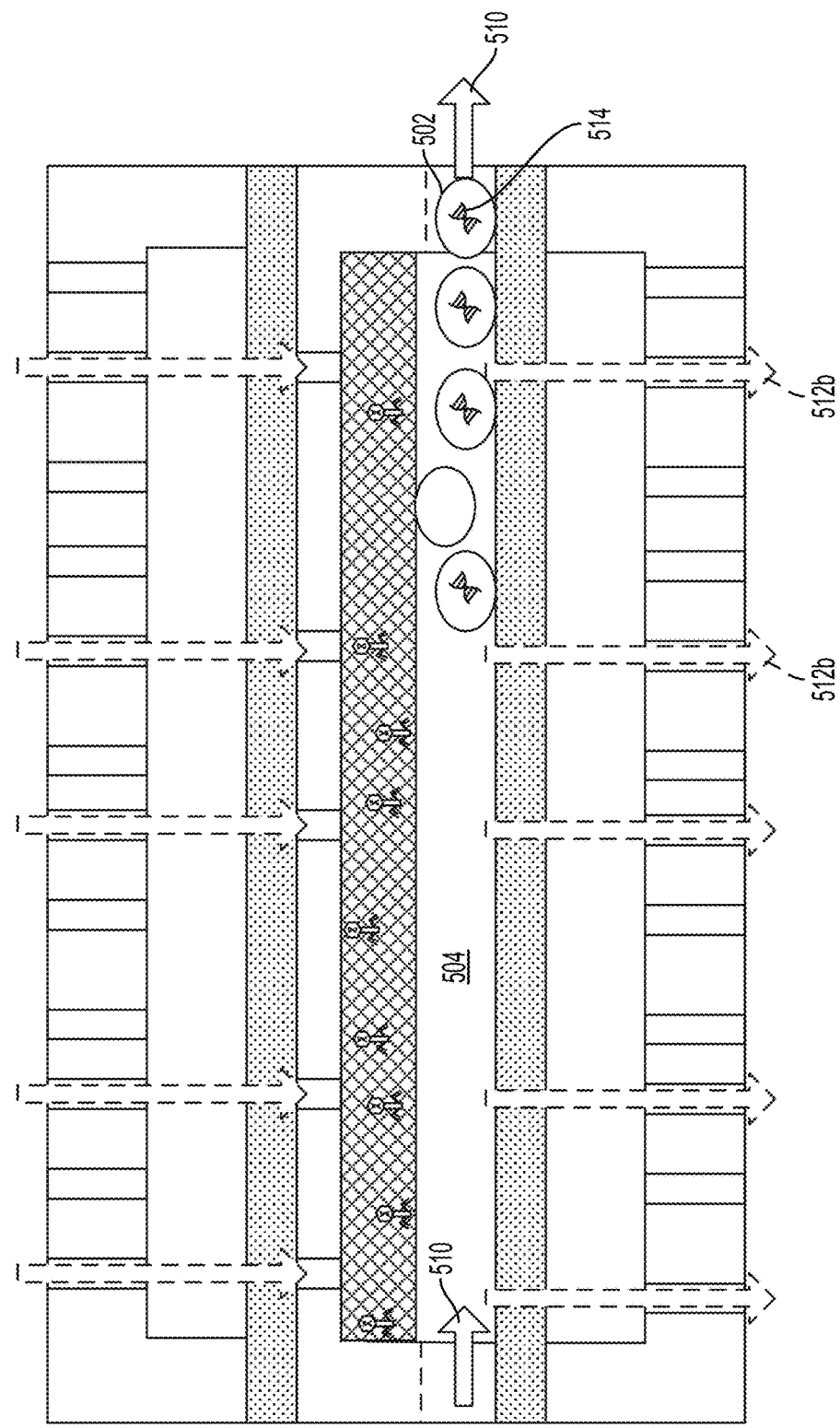

After the dwell time, the direction of the vertical flow 512 is reversed to form a reverse vertical flow 512b. The reverse vertical flow 512b releases the cells from the gel or mesh 506 (step 408) and washes away any genetic information introduction agents that may have been dislodged from the gel or mesh 506. The release step (step 408) is shown in FIG. 5C. As can be seen in FIG. 5C, many if not all of the cells 502 now hold additional genetic information 514. As shown in FIG. 5D, the method 400 further includes collecting the released cells (step 410), by reinitiating horizontal flow through the flow field 504.

Figure 6:
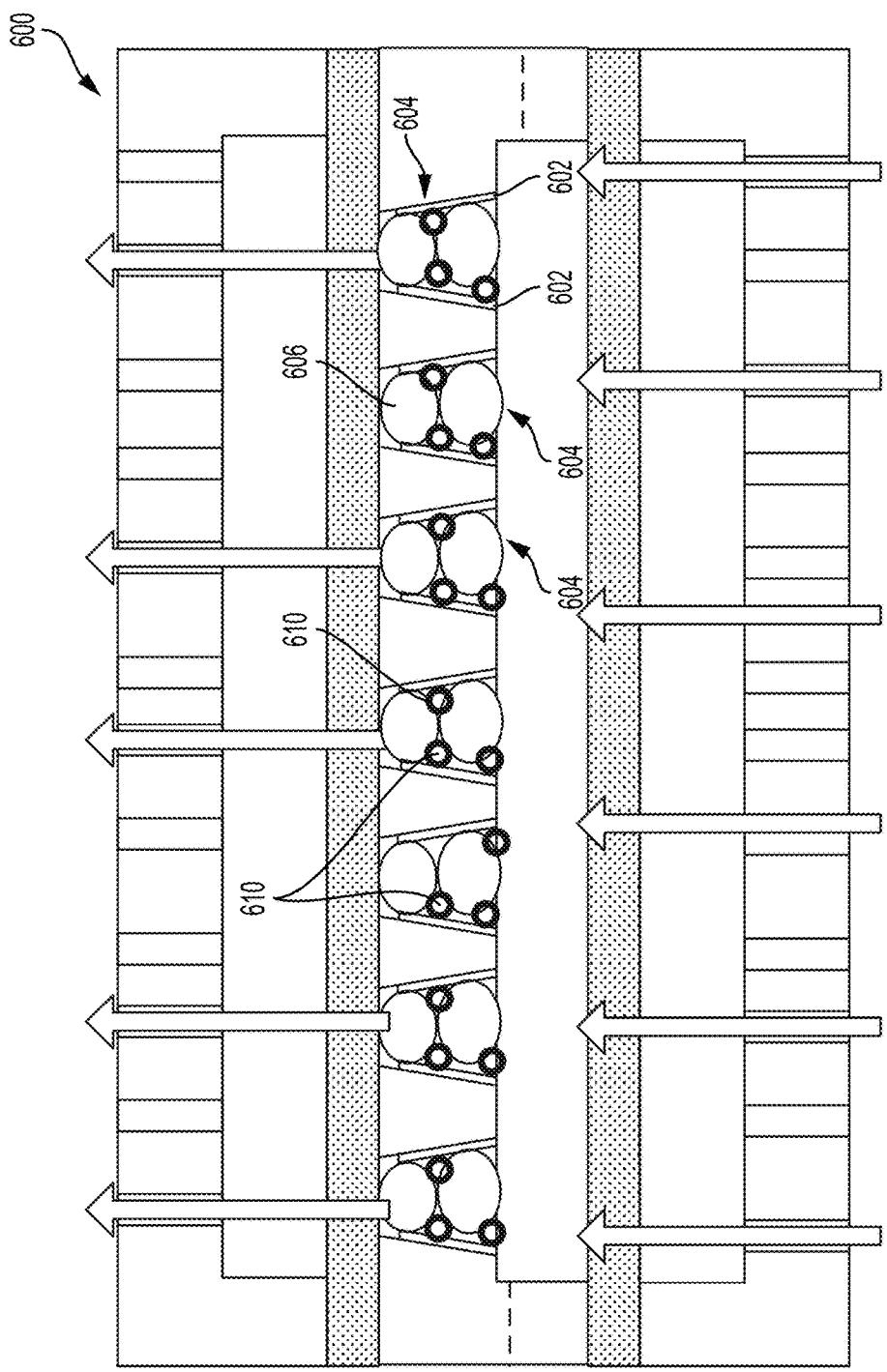
FIG. 6 shows a cross-sectional view of another example transduction stack.

FIG. 6 shows a cross-sectional view of another example transduction stack 600. The transduction stack 600 is similar to the transduction stack 102 shown in FIGS. 3A-3E. However, the transduction stack 600 includes the additional features of electroporation electrodes 602 disposed on the walls of its cell entrainment cavities 604. If a sufficient voltage is applied across the electrodes 602 while cells 606 are entrained in the cavities 604, the cell membranes of the cells 604 will temporarily become more permeable, allowing a more passive introduction of genetic material, such as plasmids 610, CRISPR complexes, lipid nanoparticles or other nucleic acid or synthetic nucleic acid vectors.

Figure 7A:
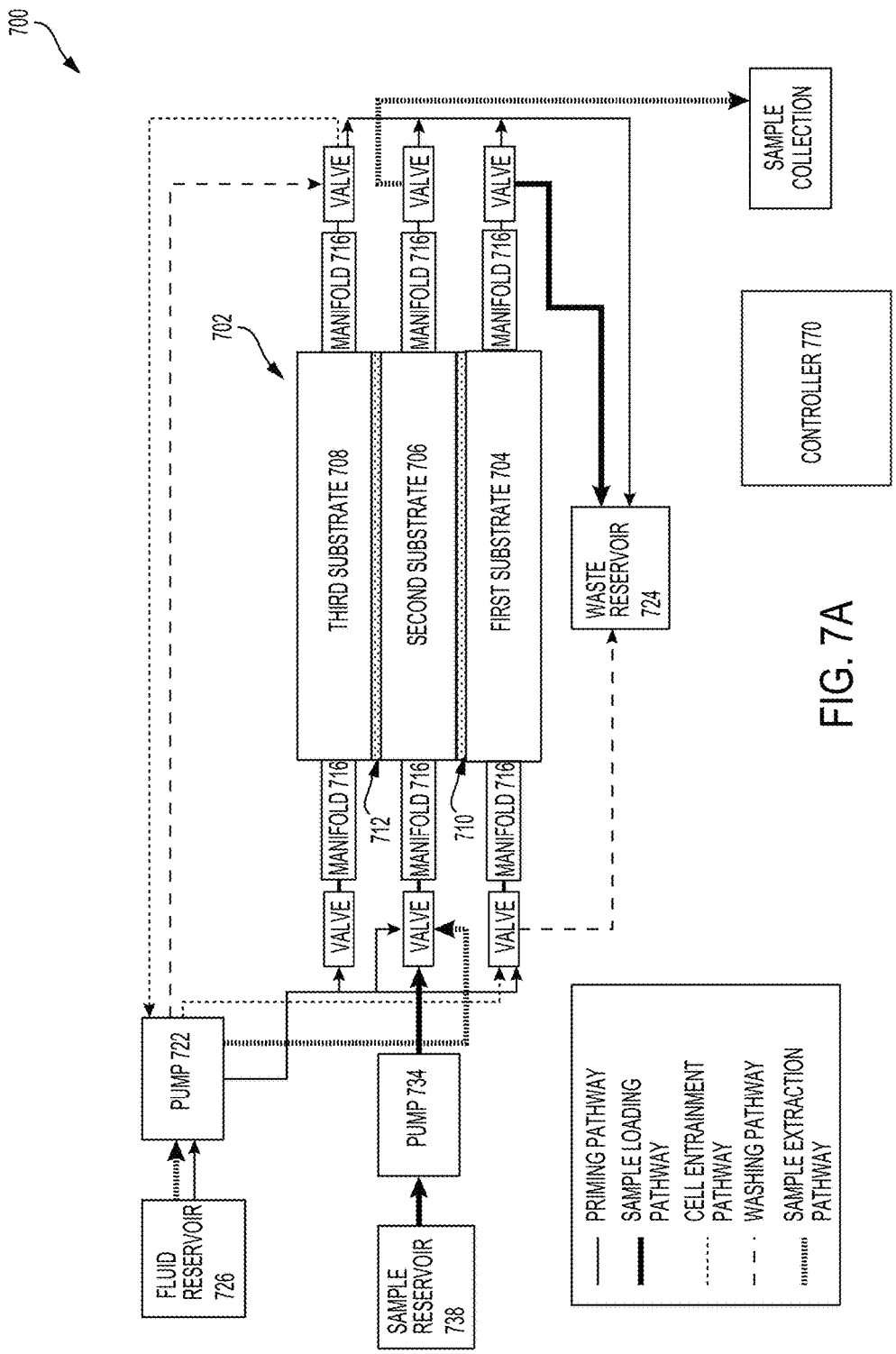
FIGS. 7A-7D show various views of another example implementation of a cell transduction system.
Figure 7B:
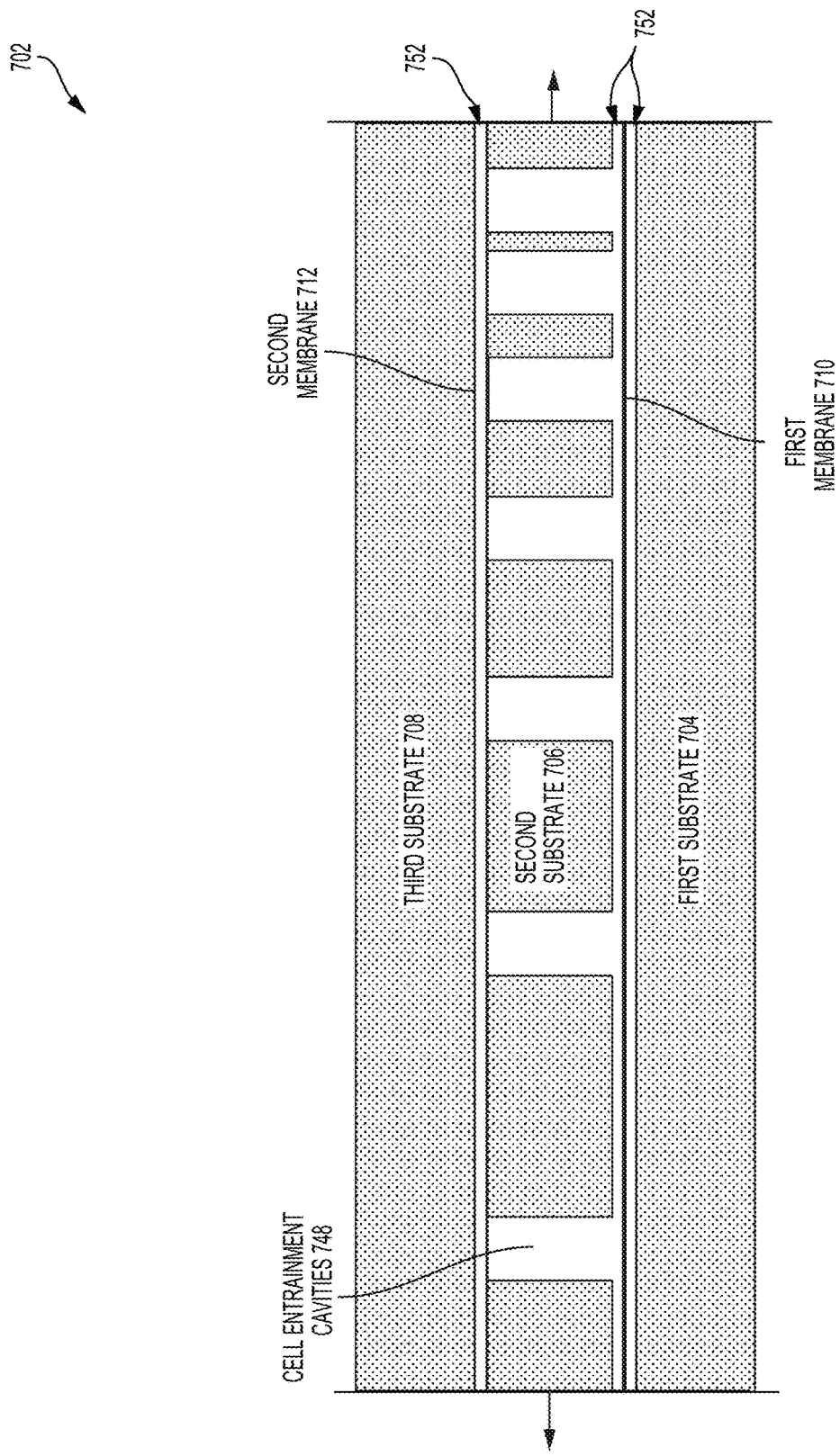
Figure 7C:
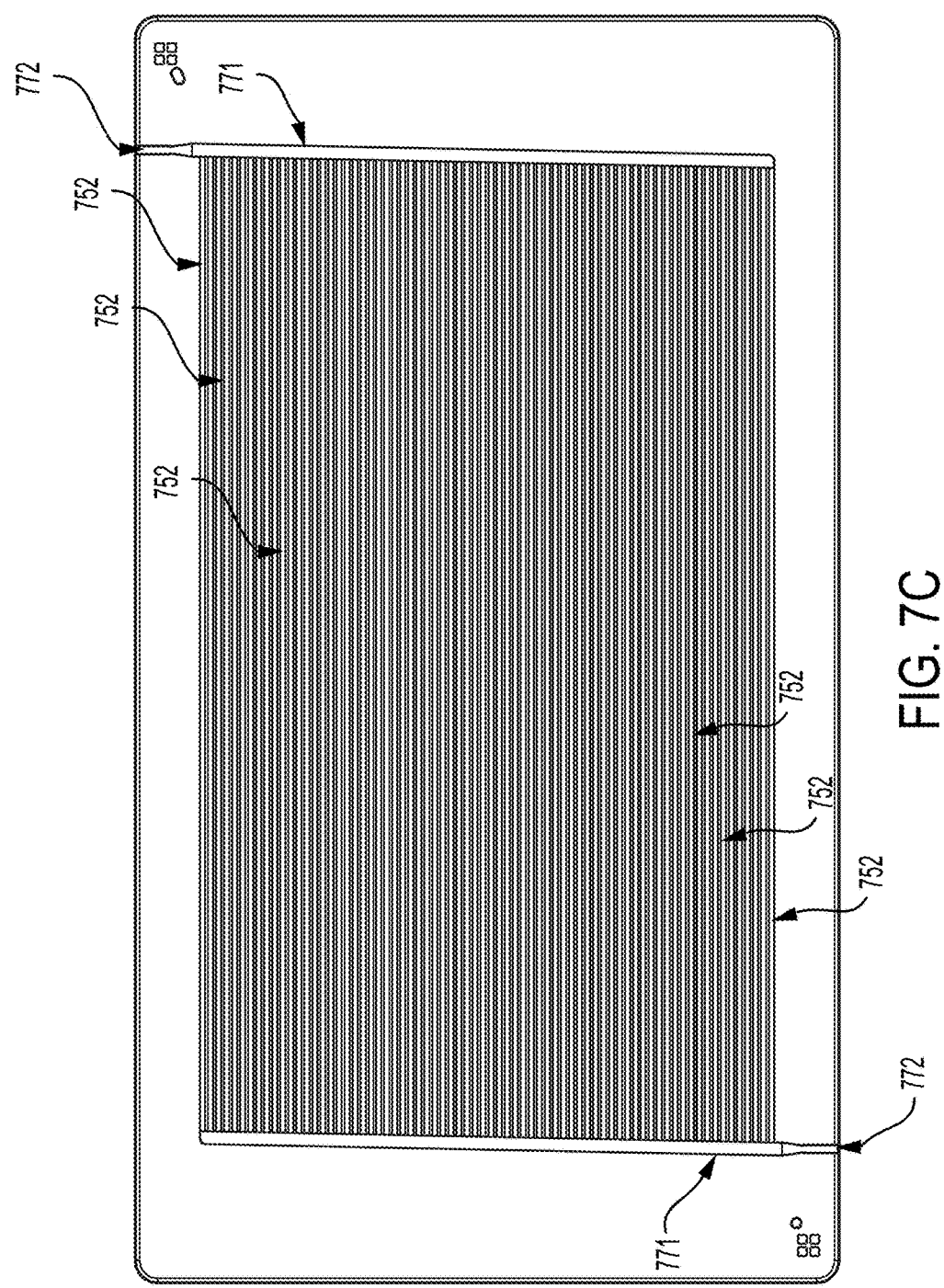
Figure 7D:
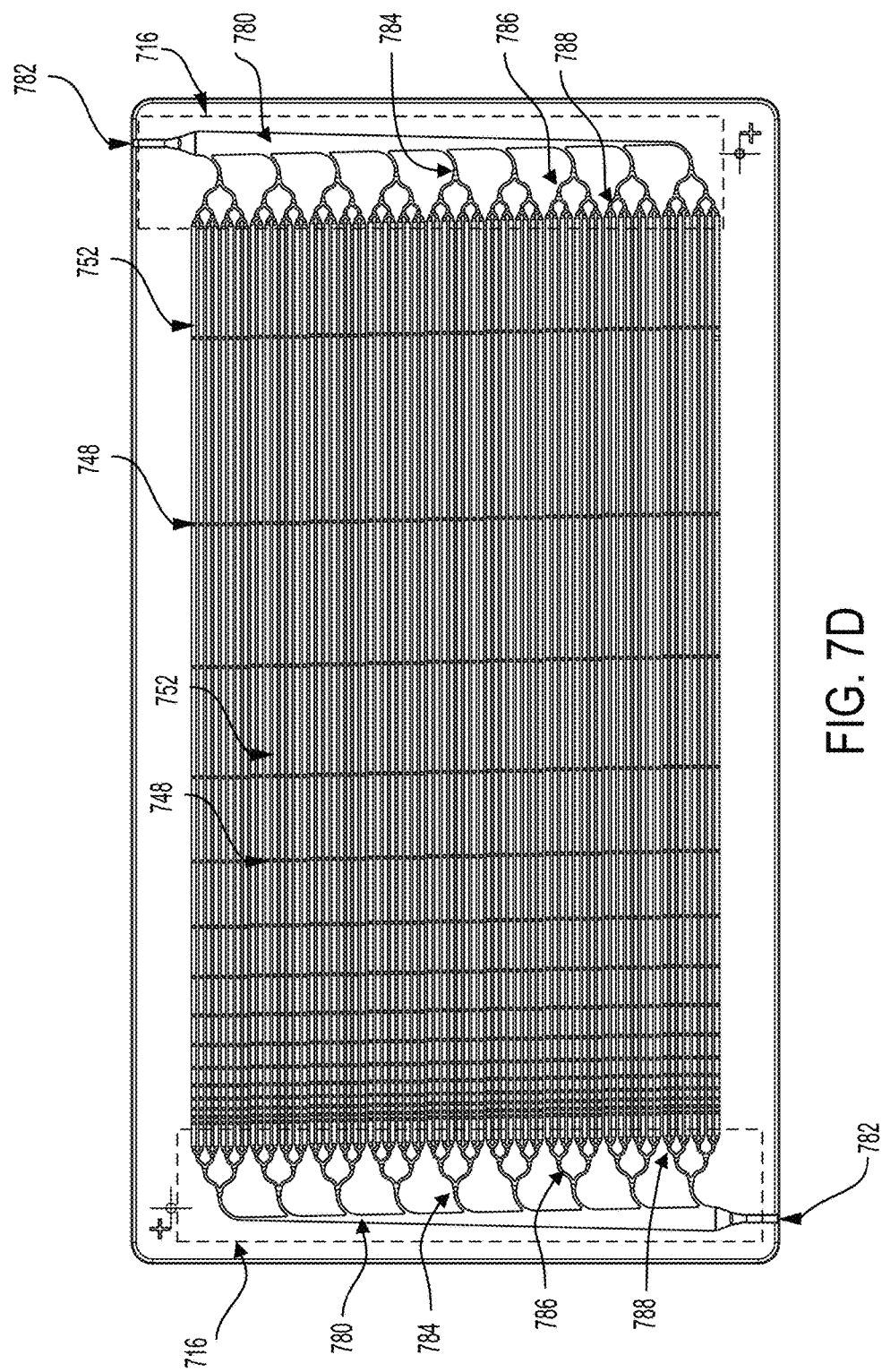

FIGS. 7A-7D show various views of another example implementation of a cell transduction system 700. FIG. 7A is a block diagram of the example cell transduction system 700. FIG. 7B is a cross-sectional view of an example cell transduction stack 702 suitable for inclusion in the cell transduction system 700. FIG. 7C shows a plan view of an example substrate suitable for use as the first or third substrates 704 and 708 in the cell transduction stack 702. FIG. 7D shows a plan view of an example second substrate 706 suitable for use in the transduction stack 702. The cell transduction system can be operated, in some implementations, according to the method 200, shown in FIG. 2.

Referring to FIG. 7A-7D and FIGS. 1A-1E, the cell transduction system 700 is similar to the cell transduction system 100 Like the cell transduction system 100, the cell transduction system includes a cell transduction stack 702 formed from three substrates, a first substrate 704, a second substrate 706, and a third substrate 708. The first substrate 704 is separated from the second substrate 706 by a first membrane 710. The second substrate 706 is separated from the third substrate 708 by a second membrane 712. The first and second membranes 710 and 712 of the cell transduction system 700 can be substantially similar to the first and second membranes 110 and 112 used in the cell transduction system 100. That is the membranes 710 and 712 can be made of the same materials described as suitable for the membranes 110 and 112, the pore sizes for the first membrane 710 can be same as those described above for the first membrane 110, and the sizes of the pores in the second membrane 712 can be the same as those described above for the second membrane 112.

Like the cell transduction system 100, the cell transduction system 700 also includes a fluid reservoir 726, a sample reservoir 738, and a waste reservoir 724, which can have similar configurations to the fluid reservoir 126, the sample reservoir 138, and the waste reservoir 124 described above. The cell transduction system 700 also includes two pumps 722 and 734 and various valves for pumping and directing fluid, cells, and genetic information introduction agents (or other additives) through the cell transduction stack 702. The pumps 722 and 734 can be controlled by a controller 770.

In contrast to the cell transduction system 100, the cell transduction system 700 lacks any vertical fluid manifolds, such as the manifolds 114 and 120. Instead, all three substrates 704, 706, and 708 include integrated horizontal fluid manifolds 716 at both ends. As described above, an integrated fluid manifold refers to a fluid manifold formed in the same substrate as a set of flow chambers of the device, instead of being formed in a separate distinct substrate or other component. In addition, as can be seen best in FIGS. 7C and 7D, the flow chambers in the first, second, and third substrates 704, 706, and 708 are formed from multiple parallel fluid channels 752, instead of single, wider flow fields 142, 144, and 146 shown in FIG. 1E.

The various routes that fluid, cells, and genetic information introduction agents (or other additives) are directed through the cell transduction system 700 are also shown in FIG. 7A. These include a priming pathway through which the system 700 is primed with buffer and then with cell media prior to introduction of cells or genetic information introduction agents (and/or other additives) and a sample loading pathway via which cells and genetic information introduction agents (and/or other additives) are loaded into the transduction stack 702. FIG. 7A also shows a cell entrainment pathway via which fluid, such as cell media, is flowed vertically (i.e., normal to the planes of the first, second, and third substrates 704, 706, and 708) through the transduction stack 702 to entrain the cells and the genetic information introduction agents (or other additives) in cell entrainment cavities 748 (shown, for example, in FIGS. 7B and 7D). FIG. 7A also shows a washing pathway via which a fluid, such as cell media, is flowed along a reversed vertical flow through the transduction stack 702 to release the cells from the cell entrainment cavities 748 and to wash the genetic information introduction agents (or other additives) from the released cells, through the first membrane 710, and into the waste reservoir 724. Finally, a cell extraction pathway is shown via which the washed cells can be removed from the cell transduction stack 702 and collected in a sample collection reservoir 740.

FIG. 7B shows a cross section of an example cell transduction stack 702 suitable for use in the cell transduction system 700. The cross section is taken along the length of the cell transduction stack 702 (i.e., from left to right across the transduction stack 702 shown in FIG. 7A). The cross-sectional view cuts through a flow channel formed in each the first, second, and third substrates 704, 706, and 708 and several cell entrainment cavities 748. Each of the substrates 704, 706, and 708 can range from about 0.5 mm to about 4 mm thick. In some implementations, the substrates 704, 706, and 708 are between about 0.5 and about 2.0 mm thick. The substrates 704, 706, and 708 can have lengths and widths than range from about 5.0 cm to about 25 cm. In some implementations, the substrates 704, 706, and 708 have roughly equal lengths and widths. In some implementations, the substrates 704, 706, and 708 can be between 50%-200% longer (i.e., parallel to the axes of the fluid channels 752) than they are wide (i.e., normal to the axes of the fluid channels 752). In some implementations, the substrates 704, 706, and 708 are wider than they are long.

The fluid channels 752 formed in the first substrate 704 can be between about 100 microns and about 200 microns (for example, about 140 microns) deep, between about 50 microns and 1.0 mm (for example, about 800 microns) wide, and between about 10 cm to about 20 cm (for example, about 15 cm) long. The fluid channels 752 formed in the second substrate 706 can have similar lengths and widths to the fluid channels 752 formed in the first substrate 704, but, in some implementations, are shallower. For example, the fluid channels 752 formed in the second substrate 706 can have depths between about 50 microns and 150 microns (e.g., between about 60 microns and about 70 microns). The fluid channels 752 in the third substrate 708, in some implementations, have the same dimensions as the fluid channels 752 in the first substrate 704.

As shown in FIG. 7B, the fluid entrainment cavities 748 can be distributed unevenly along the length of the second substrate 706. For example, the distance between adjacent cell entrainment cavities 748 along the length of the fluid channels 752 of the second substrate 706 can decrease towards the distal (with respect to the cell entrainment pathway shown in FIG. 7A) end of the transduction stack 702. The cell entrainment cavities can be circular, square, or any other regular or irregular shape sized to fit between one and about a million cells. For example, in the implementation shown in FIG. 7B, cell entrainment cavities can have a diameter or width that is less than or about equal to the width of the channels 752, in the range, for example, between about 500 microns to 1.0 mm (e.g., about 660 microns). The cell entrainment cavities 748 open on one onto the fluid channels 752 of the second substrate 706 and pass through the remaining of thickness of the second substrate 706.

FIG. 7C shows a plan view of an example substrate suitable for use as the first and third substrates 704 and 708 of the cell transduction stack 702 shown in FIG. 7A. As shown in FIG. 7C, the example substrate includes integrated manifolds 716 at either end, connected by fluid channels 752. The integrated manifolds 716 are formed from a primary channel 771 that runs substantially normal to the fluid channels 752 with a port 772 along the length of the substrate to which the fluidics shown in FIG. 7A can couple. The fluid channels 752 couple directly into the primary channel 771.

FIG. 7D shows a plan view of an example substrate suitable for use as the second substrate 706 of the cell transduction stack 702 shown in FIG. 7A. As the fluid channels 752 of the second substrate are designed to carry cells and genetic information introduction agents or other additives that are often sensitive to high levels of shear and/or high shear gradients, the second substrate 706 includes integrated manifolds 716 with more complex geometries than those included in the substrates forming the first and third substrates 704 and 706 of the cell transduction stack 702. The manifolds shown in FIG. 7D include primary channels 780 that run substantially normal to the fluid channels 752 formed in the substrate. The primary channels 780 end, at one end, at a fluid port 782 along the length of the substrate, and to which the fluidics of the cell transduction system 700 shown in FIG. 7A can couple. The primary channels 780 narrow as they near their ends furthers from the fluid ports 782, as secondary channels 784 branch off from the primary channel 780. The second channels 784 then bifurcate into tertiary and quarternary channels 786 and 788, until they finally bifurcate into the fluid channels 752 of the substrate. Further details for such a manifold can be found in U.S. Pat. No. 9,421,315, the entirety of which is incorporated by reference.

Experimental Results

Figure 8:
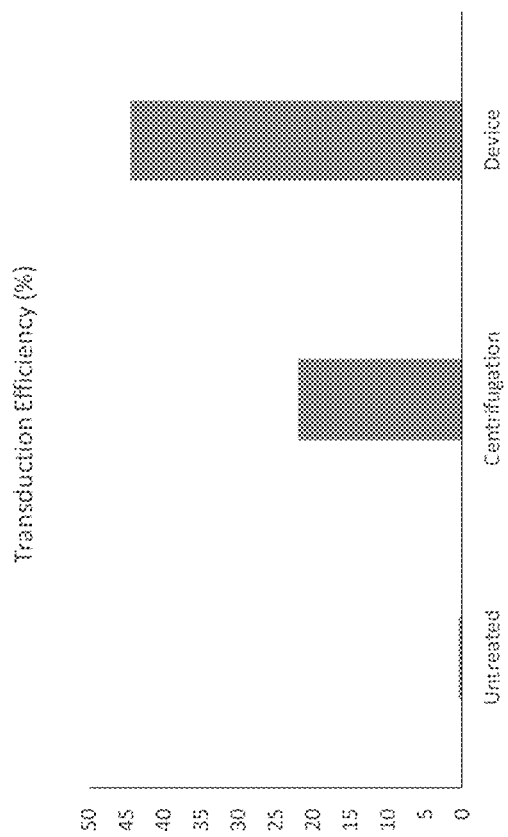
FIG. 8 shows experimental results of executing the method shown in FIG. 2 using a cell transduction system similar to that shown in FIGS. 7A-7D.

A cell transduction system having the configuration shown in FIGS. 7A-7D was tested in comparison to traditional spinoculation transduction techniques to evaluate the transduction efficiency of the system. FIG. 8 shows the results of the experiments.

In the experiment, one million cells derived from an immortalized human T-lymphocyte cell-line (Jurkat cells), which were suspended in cell media, were introduced into the device of FIGS. 7A-7D along the sample loading pathway shown in FIG. 7A. The cells were entrained within the cell entrainment cavities 748 by flowing media (RPMI, supplemented with 10% fetal bovine serum (FBS) and antibiotics (P/S)) containing a commercial lentiviral vector encoding green fluorescent protein (GFP) with a vertical flow rate maintained at 0.1 ml/min for 30 min. The vertical flow passed through the cell transduction system 700 along the cell entrainment pathway shown in FIG. 7A. The cells were then washed in the device for 10 minutes with a reverse vertical flow (at a flow rate of 0.1 ml/min) using fresh media. For control samples, one million Jurkat cells were spinoculated (e.g., centrifugally inoculated) at 800G for 30 min with commercially-available lentiviral vector encoding GFP, in accordance with a standard protocol for spinoculation of lentiviral vectors. The multiplicity of infection (MOI) in both instances was 3.0. Negative control samples were incubated without a vector.

Following treatment with the GFP+ lentiviral vector, cells were removed from the device (in the case of experimental samples) or the spinoculation tubes (in the case of control samples). The cells were re-suspended in fresh RPMI media and cultured for four days under standard cell culture conditions. The cultured cells were analyzed using flow cytometry using forward and side scatter to assess efficiency of gene transduction in cells. The results are expressed in FIG. 8 as percentages of lentiviral-tranduced GFP+ cells in the total population of viable cells.

As shown in FIG. 8, the devices of the disclosure are useful in the transduction of exogenous genetic material using suitable vectors, such as, for example, lentiviral vectors. For instance, Jurkat cells treated with the lentiviral vectors in the devices of the disclosure were stably or transiently transduced with the viral construct and the transduced cells expressed measurable quantities of the marker protein (GFP), which expression was maintained for at least 4 days post-treatment with the viral vector. Furthermore, the expression of the marker protein was specific to virally-transduced cells, as control cells expressed negligible amount of the marker protein. The results further show that the devices are effective in transducing suspended cells, which are generally more difficult to transduce compared to adherent cells.

More importantly, the results demonstrate that the devices of the disclosure confer greater transduction efficiency compared to spinoculation methods. As shown in FIG. 8, about 45% of the cells were transduced with the lentiviral vector using the device of the instant disclosure. In comparison, the transduction efficiency achieved with a routine spinoculation procedure was appreciably lower, at about 23%. The results demonstrate that the devices of the disclosure confer a significant improvement (about 100%) in the overall transduction rates compared to spinoculation methods. Accordingly, the results show that the devices of the disclosure confer significant advantages over existing systems and methods for gene delivery into target cells. It should be further noted that the devices of the disclosure improve transduction efficiency without compromising cell viability.

While this specification contains many specific implementation details, these should not be construed as limitations on the scope of any inventions or of what may be claimed, but rather as descriptions of features specific to particular implementations of particular inventions. Certain features that are described in this specification, in the context of separate implementations, can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described components and systems can generally be integrated together in a single product or packaged into multiple products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements. Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. An apparatus comprising:
a first substrate defining at least one first flow chamber coupled to a first fluid manifold;
a second substrate defining a cell entrainment layer, the cell entrainment layer including:
at least one second flow chamber;
a plurality of cell entrainment cavities, wherein each of the cell entrainment cavities opens at one end into one of the at least one second flow chambers, extends through the second substrate, and is sized to hold at least one cell;
at least one inlet to the at least one second flow chamber substantially within the plane of the second substrate; and
at least one outlet from the at least one second flow chamber substantially within the plane of the second substrate;
a first membrane positioned between the first substrate and the second substrate, the first membrane includes a plurality of pores that are small enough to prevent the passage of cells and large enough to allow the passage of a virus;
a third substrate defining at least one third flow chamber coupled to a second fluid manifold; and
a second membrane positioned between the second substrate and the third substrate, the membrane includes a second plurality of pores that are small enough to prevent the passage of viral particles but large enough to allow the passage of cell media.

2. The apparatus of claim 1, wherein the at least one first flow chamber, the at least one second flow chamber, and/or the at least one third flow chamber comprise a respective substantially planar flow field that couples to a corresponding manifold via a plurality of fluid connections.

3. The apparatus of claim 1, wherein the at least one first flow chamber, the at least one second flow chamber, and/or the at least one third flow chamber comprise a plurality of flow channels, wherein each flow channel couples to a manifold via a single fluid connection.

4. The apparatus of claim 1, further comprising the first and second fluid manifolds, wherein:
a first end of the first fluid manifold couples to the at least one first fluid chamber defined by the first substrate;
a first end of the second fluid manifold couples to the at least one third fluid chamber defined by the third substrate; and
a second end of the first fluid manifold is fluidically coupled to a second end of the second fluid manifold such that fluid can circulate through the first fluid manifold, the first membrane, the plurality of cell entrainment cavities, the second membrane, the second fluid manifold and back to the first fluid manifold.

5. The apparatus of claim 4, wherein at least one of the first fluid manifold and the second fluid manifold comprises a vertical flow manifold.

6. The apparatus of claim 4, wherein at least one of the first fluid manifold and the second fluid manifold comprises a horizontal flow manifold.

7. The apparatus of claim 4, further comprising a waste channel coupled between the second end of the first fluid manifold and the second fluid manifold by a valve, wherein the valve is configured to selectively divert fluid flow directed out of the second end of the first fluid manifold to a waste reservoir.

8. The apparatus of claim 4, further comprising a first pump configured to pump fluid into the second end of the first fluid manifold.

9. The apparatus of claim 8, comprising a second pump configured to pump fluid into the second end of the second fluid manifold, and wherein the second pump is the same pump as the first pump or different than the first pump.

10. The apparatus of claim 4, wherein the first substrate further comprises an outlet coupled to a distal end of the at least one first fluid chamber.

11. The apparatus of claim 1, wherein the cell entrainment cavities have a greater density towards a distal end of the at least one second fluid chambers than towards a proximal end of the at least one second fluid chambers.

12. A method of cell transduction comprising:
introducing cells into at least one first flow chamber;
introducing genetic information introduction agents into the first flow chamber;
flowing a first fluid in a first direction substantially normal to the at least one first flow chamber and through a plurality of cell entrainment cavities distributed along the at least one first flow chamber having proximal ends open to respective first flow chambers, thereby entraining the introduced cells and genetic information introduction agents into the plurality of cell entrainment cavities for a first period of time, thereby allowing the genetic information carried by the genetic information introduction agents to be transduced into the entrained cells;
preventing passage, through distal ends of the cell entrainment cavities, of the cells and the genetic information introduction agents;
reversing the direction of flow of the first fluid for a second period of time, thereby releasing the cells from the cell entrainment cavities and washing the genetic information introduction agents away from the cells;
flowing the released cells out of the at least one first flow chamber for collection.

13. The method of claim 12, wherein the at least one first flow chamber, the at least one second flow chamber, and/or the at least one third flow chamber comprise a respective substantially planar flow field that couples to a corresponding manifold via a plurality of fluid connections.

14. The method of claim 12, wherein the at least one first flow chamber, the at least one second flow chamber, and/or the at least one third flow chamber comprise a plurality of flow channels, wherein each flow channel couples to a manifold via a single fluid connection.

15. The method of claim 12, wherein flowing the first fluid in the first direction comprises flowing the first fluid through a first membrane having pores sized to prevent passage of the cells but large enough to allow passage of the genetic information introduction agents.

16. The method of claim 15, wherein flowing the first fluid in the first direction further comprises flowing the first fluid through the distal end of the cell entrainment cavities through a second membrane having pores sized large enough to allow passage of first fluid and small enough to prevent passage of the genetic information introduction agents through the second membrane.

17. The method of claim 12, wherein flowing the first fluid in the first direction further comprises creating a circulating flow in which fluid flowing through the second membrane is redirected back through the first membrane in the first direction.

18. The method of claim 12, wherein the genetic information introduction agents comprise viruses.

19. The method of claim 12, wherein the cells and the genetic information introduction agents are introduced into the first flow field substantially simultaneously.

20. The method of claim 12, wherein the cells are introduced into the first flow field prior to the introduction of the genetic information introduction agents into the first flow field.

21. An apparatus comprising:
a first substrate defining at least one first flow chamber coupled to a first fluid manifold;
a second substrate defining at least one second flow chamber comprising:
a first membrane positioned between the first substrate and the second substrate, wherein
the first membrane includes a plurality of pores that are small enough to prevent the
passage of cells and large enough to allow the passage of a virus;
a third substrate defining a third flow chamber and coupled to a second fluid manifold;
a second membrane positioned between the second substrate and the third substrate, the membrane includes a second plurality of pores that are small enough to prevent the passage of viral particles but large enough to allow the passage of cell media;
and a means for entraining cells within the at least one second flow chamber as a result of a flow of fluid across the first and second membranes.

22. The apparatus of claim 21, wherein the means for entraining cells comprises the second membrane.

23. The apparatus of claim 21, wherein the second membrane comprises one of a patterned membrane and an unpatterned membrane.

* * * * *